(12) United States Patent
Bang et al.

(10) Patent No.: US 12,414,918 B2
(45) Date of Patent: Sep. 16, 2025

(54) PHARMACEUTICAL COMPOSITION OF LIPID NANOPARTICLE FOR DELIVERING NUCLEIC ACID DRUG CONTAINING TREHALOSE DERIVATIVE AND NOVEL STRUCTURE-MAINTAINING LIPID COMPOUND

(71) Applicant: SML BIOPHARM CO., LTD., Gwangmyeong-si (KR)

(72) Inventors: Eun Kyoung Bang, Seoul (KR); Gyo Chang Keum, Seoul (KR); Taek Kang, Seoul (KR); Byung Sun Jeon, Seoul (KR); An Soo Lee, Seoul (KR); Jae Hwan Nam, Bucheon-si (KR); Seo Hyeon Bae, Gimhae-si (KR)

(73) Assignee: SML BIOPHARM CO., LTD., Gyeonggi-Do (KR)

( * ) Notice: Subject to any disclaimer, the term of this patent is extended or adjusted under 35 U.S.C. 154(b) by 329 days.

(21) Appl. No.: 17/676,822

(22) Filed: Feb. 22, 2022

(65) Prior Publication Data
US 2023/0149311 A1    May 18, 2023

(30) Foreign Application Priority Data
Nov. 10, 2021    (KR) .......................... 10-2021-0153940

(51) Int. Cl.
*A61K 9/16*    (2006.01)
*B82Y 5/00*    (2011.01)

(52) U.S. Cl.
CPC .............. *A61K 9/1623* (2013.01); *B82Y 5/00* (2013.01)

(58) Field of Classification Search
None
See application file for complete search history.

(56) References Cited

U.S. PATENT DOCUMENTS

| | | | |
|---|---|---|---|
| 8,058,069 B2 | 11/2011 | Yaworski et al. | |
| 9,364,435 B2 | 6/2016 | Yaworski et al. | |
| 2014/0178475 A1* | 6/2014 | Figueiredo | A61K 47/10 514/252.19 |

FOREIGN PATENT DOCUMENTS

| | | |
|---|---|---|
| JP | 2020-073568 A | 5/2020 |
| KR | 10-1967417 B1 | 4/2019 |
| KR | 10-2019-0132405 A | 11/2019 |
| WO | 2009/127060 A1 | 10/2009 |
| WO | 2010/054401 A1 | 5/2010 |
| WO | 2010/129709 A1 | 11/2010 |
| WO | 2010/144740 A1 | 12/2010 |
| WO | 2012/000104 A1 | 1/2012 |
| WO | 2015/161218 A1 | 10/2015 |
| WO | 2018/081480 A1 | 5/2018 |
| WO | 2020/232276 A1 | 11/2020 |

OTHER PUBLICATIONS

Hou et al. (Nature Reviews Materials 6, 1078-1094 (published Aug. 10, 2021).*
Pengxuan Zhao et al., "Long-term storage of lipid-like nanoparticles for mRNA delivery," Bioactive Materials, 2020, pp. 358-363, vol. 5, Issue 2.
Danielle Irby et al., "Lipid-Drug Conjugate for Enhancing Drug Delivery," Mol Pharm., May 1, 2017, 1325-1338.
Nawal K. Paul et al., "Direct Synthesis of Maradolipids and Other Trehalose 6-Monoesters and 6,6'-Diesters," The Journal of Organic Chemistry, 2012, 22 pages.
Siddharth Patel et al., "Naturally occurring cholesterol analogues in lipid nanoparticles induce polymorphic shape and enhance intracellular delivery of mRNA," Nat. Commun., 2020, 13 pages.
S. Trombino et al., "Solid lipid nanoparticles made of trehalose monooleate for cyclosporin—A topic release", Journal of Drug Delivery Science and Technology, 2019, pp. 563-569, vol. 49.
E. Colombo et al., "Nanolipid-trehalose conjugates and nano-assemblies as putative autophagy inducers", Pharmaceutics. Aug. 20, 2019, 17 pages.

* cited by examiner

*Primary Examiner* — Anna R Falkowitz
*Assistant Examiner* — Garen Gotfredson
(74) *Attorney, Agent, or Firm* — CANTOR COLBURN LLP

(57) ABSTRACT

Disclosed is a novel composition of lipid nanoparticles for stabilizing a nucleic acid drug and enhancing delivery in vivo. Lipid nanoparticles include a nucleic acid drug and a lipid, and the nucleic acid includes all of mRNA-based vaccines, RNA for immune boosters, miRNA, siRNA, pDNA, antisense ODN, and pDNA. The lipid of nanoparticles includes a trehalose-based lipid, an ionizable lipid, a phospholipid, a PEG-lipid, and a structure-maintaining lipid. The structure-maintaining lipid provides a composition that can replace commonly used cholesterol with a lithocholic acid derivative, a glycyrrhetinic acid derivative, or a diosgenin derivative. The lipid nanoparticles can be used as a vaccine or therapeutic agent, depending on the type of nucleic acid drug that is used.

18 Claims, 4 Drawing Sheets

PHARMACEUTICAL COMPOSITION OF LIPID NANOPARTICLE FOR DELIVERING NUCLEIC ACID DRUG CONTAINING TREHALOSE DERIVATIVE AND NOVEL STRUCTURE-MAINTAINING LIPID COMPOUND

CROSS-REFERENCE TO RELATED APPLICATION

This application claims under 35 U.S.C. § 119(a) the benefit of priority to Korean Patent Application No. 10-2021-0153940, filed on Nov. 10, 2021, the entire contents of which are incorporated herein by reference.

BACKGROUND

(a) Technical Field

The present invention relates to a lipid nanoparticle composition for stabilizing and delivering a nucleic acid drug, and more particularly to a lipid nanoparticle composition containing a lipid including trehalose and a lithocholic acid derivative, a glycyrrhetinic acid derivative, or diosgenin derivative as a cholesterol substitute.

(b) Background Art

Vaccines that prevent diseases using the immune action of the human body by injecting antigens for specific diseases into the human body have long protected humankind from various infectious diseases. Various vaccine platforms are present depending on the type of antigen injection. These include live vaccines, which contain attenuated pathogens, recombinant protein vaccines which contain protein antigens, virus-like particles and the like, and DNA vaccines, RNA vaccines, viral vector vaccines, and the like, which contain antigen-encoding genes.

Among them, RNA vaccines are used in the form of administering mRNA encoding the antigen into the human body, and have advantages of avoiding problems of infection, genetic mutation, and the like and being capable of being rapidly developed, but have problems of low stability since they are easily degraded by RNases in vivo and of difficulty inducing an immune response using mRNA itself due to difficulty in delivery to cells. To overcome these problems, lipid nanoparticles have been used, and lipid nanoparticles are generally currently used in a form in which ionizable lipids, phospholipids, cholesterols, and PEG lipids are mixed at a predetermined ratio.

However, lipid nanoparticles that have been developed to date do not satisfy market requirements for stabilization and delivery of nucleic acids to improve the expression of target antigens.

PRIOR ART DOCUMENT

Patent Document (Patent Document 1) PCT International Patent No. WO 2010/144740
(Patent Document 2) PCT International Patent No. WO 2012/000104
(Patent Document 3) PCT International Patent No. WO 2010/129709
(Patent Document 4) PCT International Patent No. WO 2010/054401
(Patent Document 5) PCT International Patent No. WO 2009/127060
(Patent Document 6) U.S. Pat. No. 9,364,435
(Patent Document 7) Korean Patent No. 10-1967417
(Patent Document 8) Korean Patent Laid-open Publication No. 10-2019-0132405

Non-Patent Document (Non-patent Document 1) Direct Synthesis of Maradolipids and Other Trehalose 6-monoesters and 6,6'-diesters, N. J. Paul et al. J. Org. Chem. 2013, 78: 363
(Non-patent Document 2) Naturally-occurring cholesterol analogues in lipid nanoparticles induce polymorphic shape and enhance intracellular delivery of mRNA, S. Patel et al., Nat. Commun. 2020, 11: 983

The above information disclosed in this Background section is only for enhancement of understanding of the background of the invention, and therefore it may contain information that does not form the prior art that is already known in this country to a person of ordinary skill in the art.

SUMMARY OF THE DISCLOSURE

Accordingly, as a result of research to solve the above problems, the present inventors invented a novel lipid nanoparticle composition used to stabilize nucleic acid and enhance delivery in order to increase antigen expression efficiency. Thus, it is an object of the present invention to provide such a novel composition.

The objects of the present invention are not limited to that described above. Other objects of the present invention will be clearly understood from the following description, and are able to be implemented by means defined in the claims and combinations thereof.

In view of the objects described above, the present invention provides the following aspects.

In one aspect, the present invention provides a lipid nanoparticle composition containing a lipid component, wherein the lipid nanoparticle composition contains a trehalose derivative compound represented by the following Formula 1:

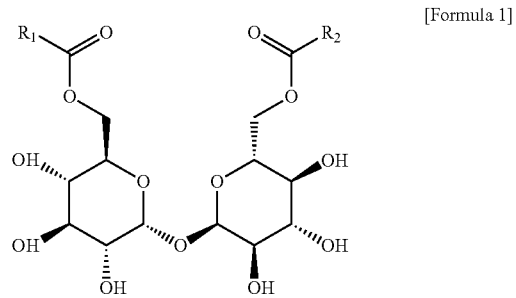

[Formula 1]

wherein $R_1$ and $R_2$ are each independently a saturated or unsaturated hydrocarbon having 2 to 20 carbon atoms.

In an embodiment, $R_1$ and $R_2$ are each independently an unsaturated hydrocarbon having 2 to 20 carbon atoms.

In an embodiment, $R_1$ and $R_2$ are each independently an alkenyl group having 6 to 20 carbon atoms and including one to three unsaturated bonds.

In an embodiment, $R_1$ and $R_2$ are each independently an alkenyl group having 10 to 20 carbon atoms and including one or more unsaturated bonds.

In an embodiment, $R_1$ and $R_2$ are each independently an alkenyl group having 14 to 20 carbon atoms and including one unsaturated bond.

In an embodiment, the trehalose derivative compound is a compound represented by the following Formula 2:

[Formula 2]

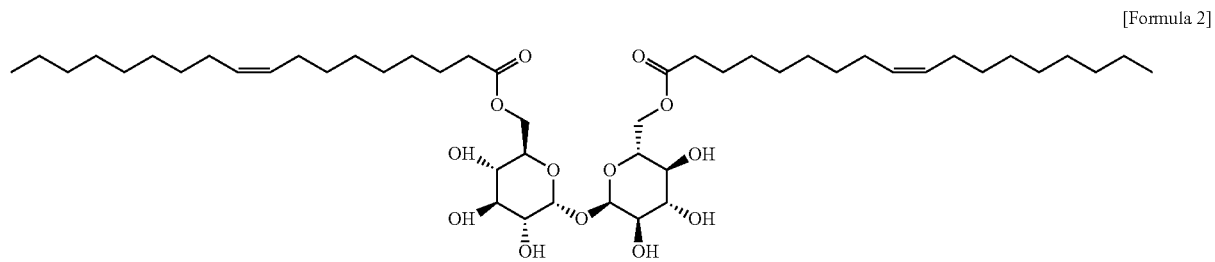 [SMILES: CCCCCCCC/C=C\CCCCCCCC(=O)OC[C@H]1O[C@H](O[C@H]2O[C@H](COC(=O)CCCCCCC/C=C\CCCCCCCC)[C@@H](O)[C@H](O)[C@H]2O)[C@H](O)[C@@H](O)[C@@H]1O]

In an embodiment, the lipid nanoparticle composition does not contain a cholesterol lipid as a structural lipid.

In an embodiment, the composition contains a lithocholic acid derivative compound represented by the following Formula 3 as a structural lipid:

[Formula 3]

wherein $R_3$ and $R_4$ are each independently hydrogen or a saturated or unsaturated hydrocarbon having 2 to 20 carbon atoms.

In an embodiment, at least one of $R_3$ and $R_4$ is a saturated or unsaturated hydrocarbon having 2 to 20 carbon atoms.

In an embodiment, in the lithocholic acid derivative compound represented by Formula 3, $R_3$ is hydrogen and $R_4$ is an alkyl group having 3 to 7 carbon atoms.

In an embodiment, the lithocholic acid derivative compound includes at least one of the following Formulas 4 to 6:

[Formula 4]

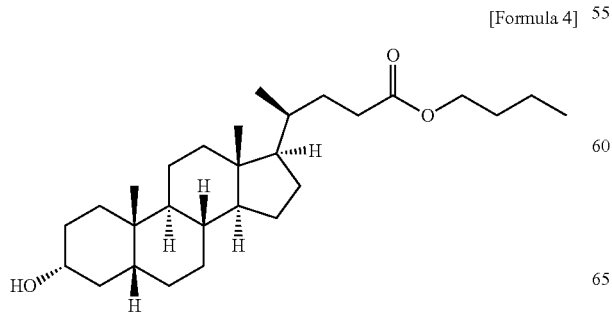

-continued

[Formula 5]

[Formula 6]

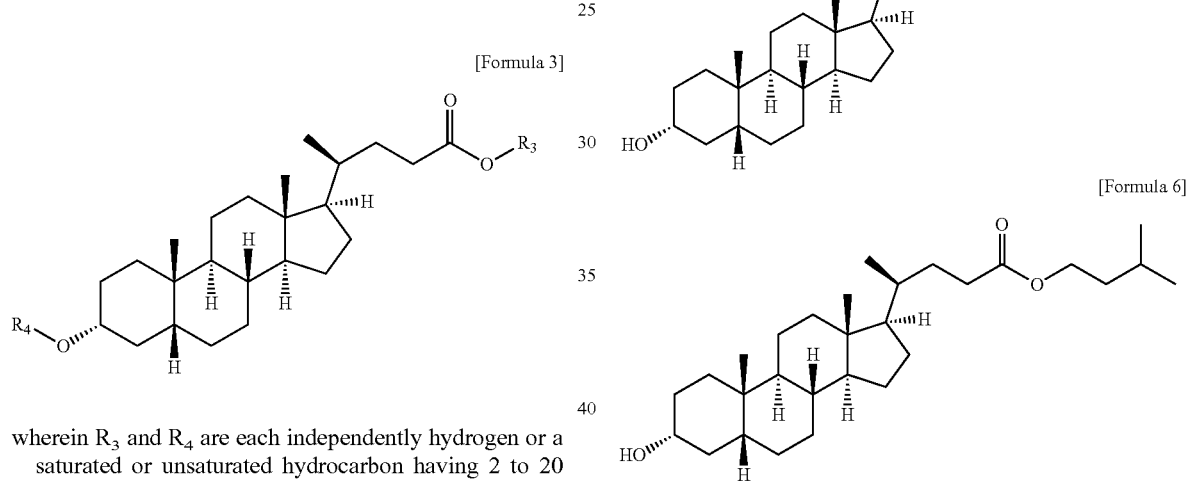

In an embodiment, the composition contains a glycyrrhetinic acid derivative compound represented by the following Formula 7 as a structural lipid:

[Formula 7]

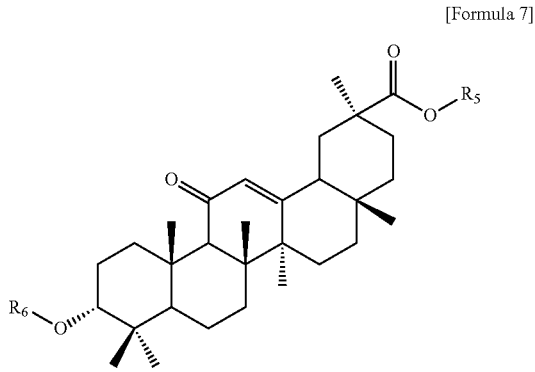

wherein $R_5$ and $R_6$ are each independently a saturated or unsaturated hydrocarbon having 2 to 20 carbon atoms.

In an embodiment, at least one of $R_5$ and $R_6$ is a saturated or unsaturated hydrocarbon having 2 to 20 carbon atoms.

In an embodiment, in the glycyrrhetinic acid derivative compound of Formula 7, $R_6$ is hydrogen, and $R_5$ is an alkyl group having 3 to 8 carbon atoms or an alkenyl group having 3 to 8 carbon atoms.

In an embodiment, the glycyrrhetinic acid derivative compound includes at least one of the following Formulas 8 to 10:

[Formula 8]

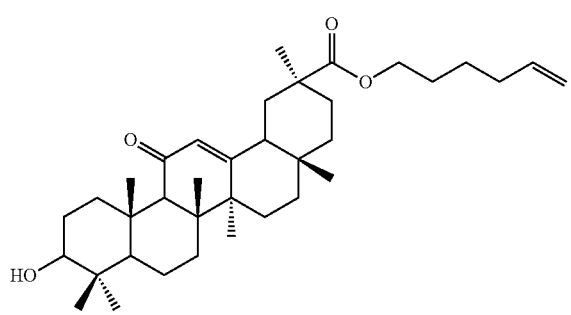

[Formula 9]

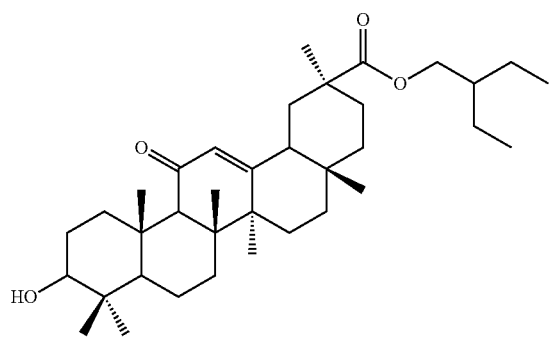

[Formula 10]

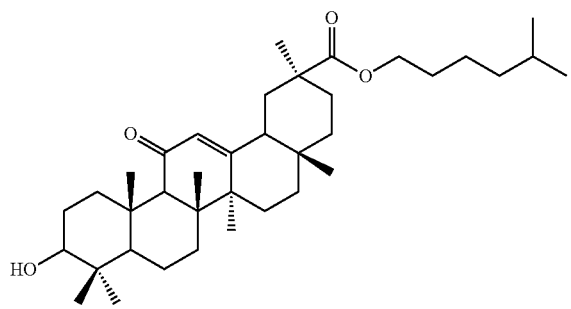

In an embodiment, the composition contains a diosgenin derivative compound represented by the following Formula 11 as a structural lipid:

[Formula 11]

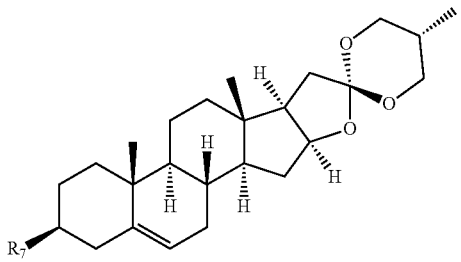

wherein $R_7$ includes —OH, —OMe, —NH$_2$, —NHMe, —NME2, —NME3, —SH, glucose, methyl, or a saturated or unsaturated hydrocarbon having 2 to 20 carbon atoms.

In an embodiment, in the diosgenin derivative compound of Formula 11, $R_7$ is a hydrogen oxide group, an amino group, or a methyl amino group.

In an embodiment, the diosgenin derivative compound includes at least one of the following Formulas 12 to 14:

[Formula 12]

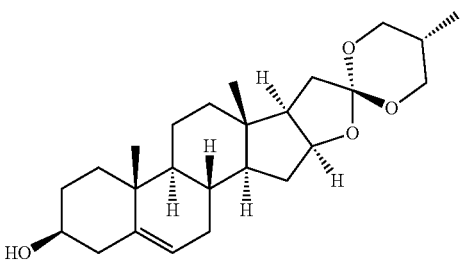

[Formula 13]

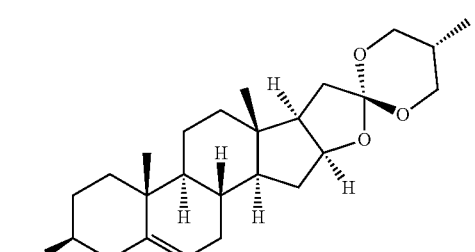

[Formula 14]

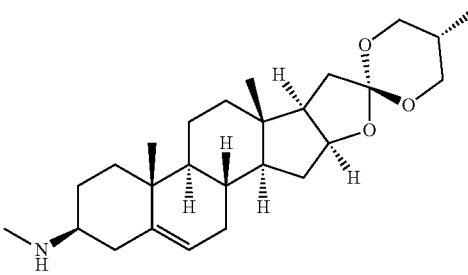

In an embodiment, the lipid nanoparticle composition contains an ionic lipid selected from the group consisting of the following compounds:

3-(didodecylamino)-N1,N1,4-tridodecyl-1-piperazineethanamine (KL10); N1-[2-(didodecylamino)ethyl]-N1,N4,N4-tridodecyl-1,4-piperazinediethanamine (KL22); 14,25-ditridecyl-15,18,21,24-tetraaza-octatriacontane (KL25); 1,2-dilinoleyloxy-N,N-dimethylaminopropane (DLin-DMA); 2,2-dilinoleyl-4-dimethylaminomethyl-[1,3]-dioxolane (DLin-K-DMA); heptatriaconta-6,9,28,31-tetraen-19-yl 4-(dimethylamino)butanoate (DLin-MC3-DMA); 2,2-dilinoleyl-4-(2-dimethylaminoethyl)-[1,3]-dioxolane (DLin-KC2-DMA); 1,2-dioleyloxy-N,N-dimethylaminopropane (DODMA); 2-({8-[(3β)-cholest-5-en-3-yloxy]octyl}oxy)-N,N-dimethyl-3-[(9Z,12Z)-octadeca-9,12-dien-1-yloxy]propan-1-amine (octyl-CLinDMA); (2R)-2-({8-[(3β)-cholest-5-en-3-yloxy]octyl}oxy)-N,N-dimethyl-3-[(9Z,12Z)-octadeca-9,12-dien-1-yloxy]propan-1-amine (octyl-CLinDMA (2R)); and (2S)-2-({8-[(3β)-cholest-5-en-3-yloxy]octyl}oxy)-N,N-dimethyl-3-[(9Z,12Z)-octadeca-9,12-dien-1-yloxy]propan-1-amine (octyl-CLinDMA (2S)).

In an embodiment, the lipid nanoparticle composition contains a phospholipid selected from the group consisting of the following compounds:
1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 diether PC), 1-oleoyl-2-cholesteryl-hemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-dioleoyl-sn-glycero-3-phosphoethanolamine (DOPE), 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), dipalmitoylphosphatidylglycerol (DPPG), palmitoyloleoylphosphatidylethanolamine (POPE), distearoyl-phosphatidyl-ethanolamine (DSPE), dipalmitoyl phosphatidyl ethanolamine (DPPE), dimyristoylphosphoethanolamine (DMPE), 1-stearoyl-2-oleoyl-phosphatidylethanol amine (SOPE), 1-stearoyl-2-oleoyl-phosphatidylcholine (SOPC), sphingomyelin, phosphatidylcholine, phosphatidylethanolamine, phosphatidylserine, phosphatidylinositol, phosphatidic acid, palmitoyloleoyl phosphatidylcholine, lysophosphatidylcholine, and lysophosphatidylethanolamine (LPE).

In an embodiment, the lipid nanoparticle composition further contains a PEG lipid selected from the group consisting of PEG-modified phosphatidylethanolamine, PEG-modified phosphatidic acid, PEG-modified ceramide, PEG-modified dialkylamine, PEG-modified diacylglycerol, PEG-modified dialkylglycerol, and mixtures thereof.

In an embodiment, the lipid nanoparticle composition further contains an ionic lipid, wherein the molar ratio of the ionic lipid to the trehalose derivative compound is 1:0.7 to 1:1.3.

In an embodiment, the lipid nanoparticle composition further contains a lithocholic acid derivative compound of the following Formula 3, a glycyrrhetinic acid derivative compound of the following Formula 7, or a diosgenin derivative compound represented by the following Formula 11 as a structural lipid, wherein the molar ratio of the ionic lipid to the trehalose derivative compound to the structural lipid is 1:0.70-1.30:1.30-1.8:

[Formula 3]

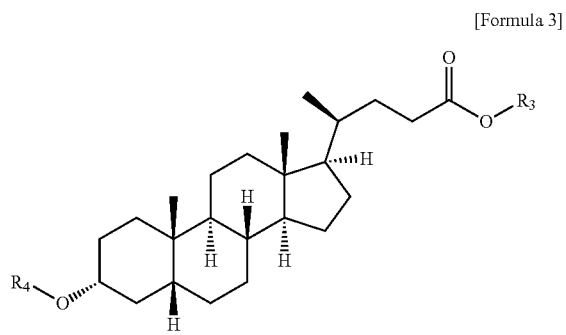

wherein $R_3$ and $R_4$ are each independently hydrogen or a saturated or unsaturated hydrocarbon having 2 to 20 carbon atoms,

[Formula 7]

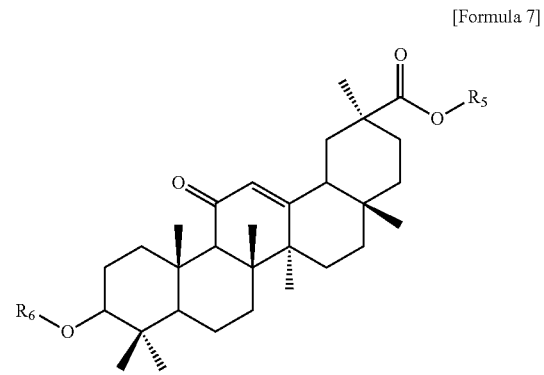

wherein $R_5$ and $R_6$ are each independently hydrogen or a saturated or unsaturated hydrocarbon having 2 to 20 carbon atoms.

[Formula 11]

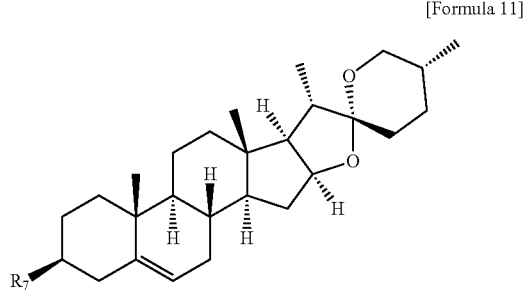

wherein $R_7$ includes —OH, —OMe, —NH$_2$, —NHMe, —NME2, —NME3, —SH, -glucose, methyl, or a saturated or unsaturated hydrocarbon having 2 to 20 carbon atoms.

In an embodiment, the lipid nanoparticle composition further contains a phospholipid, wherein the molar ratio of the ionic lipid to the trehalose derivative compound to the structural lipid to the phospholipid is 1:0.70-1.30:1.30-1.80:0.35-0.45.

In an embodiment, the lipid nanoparticle composition further contains a PEG lipid, wherein the molar ratio of the ionic lipid to the trehalose derivative compound to the structural lipid, to the phospholipid to the PEG lipid is 1:0.70-1.30:1.30-1.80:0.35-0.45:0.03-0.09.

In an embodiment, the lipid nanoparticle composition further contains an ionic lipid, a structural lipid, a phospholipid, and a PEG lipid, wherein the lipid nanoparticle composition contains 1 mol % to 59 mol % of the ionic lipid, 1 mol % to 59 mol % of the trehalose derivative compound, 30 mol % to 60 mol % of the structural lipid, 5 mol % to 20 mol % of the phospholipid, and 0.5 mol % to 5 mol % of the PEG lipid.

In an embodiment, the lipid nanoparticle composition further contains a therapeutic and/or prophylactic agent.

In an embodiment, the therapeutic and/or prophylactic agent is a vaccine or compound capable of inducing an immune response.

In an embodiment, the therapeutic and/or prophylactic agent is nucleic acid selected from the group consisting of interfering RNA (siRNA), asymmetric interfering RNA (aiRNA), microRNA (miRNA), dicer-substrate RNA (dsRNA), small hairpin RNA (shRNA), messenger RNA (mRNA), and mixtures thereof.

Other aspects and preferred embodiments of the invention are discussed infra.

BRIEF DESCRIPTION OF THE DRAWINGS

The above and other features of the present invention will now be described in detail with reference to certain exemplary embodiments thereof, illustrated in the accompanying drawings which are given hereinbelow by way of illustration only, and thus are not limitative of the present invention, and wherein.

DETAILED DESCRIPTION

Figure 1:
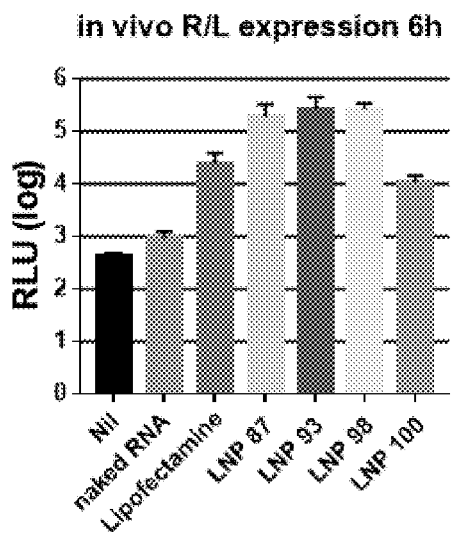
FIG. 1 illustrates the protein expression efficiency of lipid nanoparticles (LNP 87, 93, 98, 100) of a novel composition containing Renilla luciferase (R/L) mRNA, determined based on an amount of Renilla luciferase (R/L) expressed 6 hours and 24 hours after injection into the ears of mice.
Figure 1:
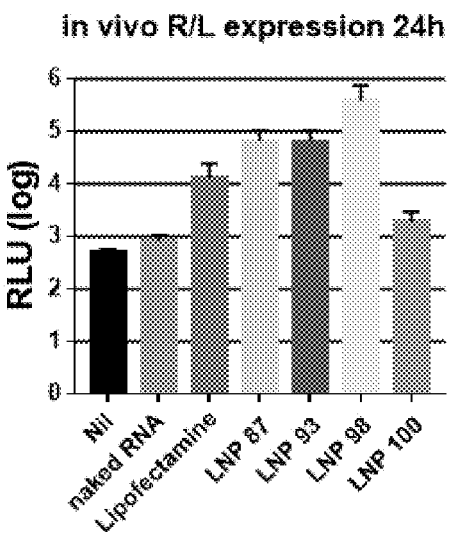

Unless the context clearly indicates otherwise, all numbers, figures, and/or expressions that represent ingredients, reaction conditions, polymer compositions, and amounts of mixtures used in the specification are approximations that reflect various uncertainties of measurement occurring inherently in obtaining these figures, among other things. For this reason, it should be understood that, in all cases, the term "about" should be understood to modify all such numbers, figures, and/or expressions. In addition, when numerical ranges are disclosed in the description, these ranges are continuous, and include all numbers from the minimum to the maximum, including the maximum within each range, unless otherwise defined. Furthermore, when the range refers to an integer, it includes all integers from the minimum to the maximum, including the maximum within the range, unless otherwise defined.

It should be understood that, in the specification, when a range is referred to regarding a parameter, the parameter encompasses all figures, including end points disclosed within the range. For example, the range of "5 to 10" includes figures of 5, 6, 7, 8, 9, and 10, as well as arbitrary sub-ranges, such as ranges of 6 to 10, 7 to 10, 6 to 9, and 7 to 9, and any figures, such as 5.5, 6.5, 7.5, 5.5 to 8.5, and 6.5 to 9, between appropriate integers that fall within the range. In addition, for example, the range of "10% to 30%" encompasses all integers that include numbers such as 10%, 11%, 12%, and 13%, as well as 30%, and any sub-ranges, such as 10% to 15%, 12% to 18%, or 20% to 30%, as well as any numbers, such as 10.5%, 15.5%, and 25.5%, between appropriate integers that fall within the range.

Hereinafter, the present invention will be described in more detail.

In one aspect, the present invention provides a novel composition of lipid nanoparticles containing a lithocholic acid derivative, glycyrrhetinic acid derivative, or diosgenin derivative, that is capable of stabilizing nucleic acid drugs and improving in-vivo delivery and of replacing cholesterol used in trehalose-based lipids and conventional lipid nanoparticles.

The present invention provides a lipid nanoparticle composition containing a trehalose-based lipid that stabilizes a nucleic acid molecule and has the structure of the following Formula 1:

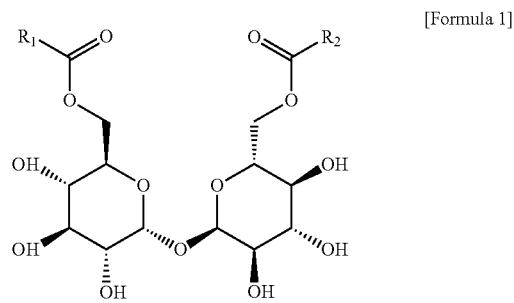

[Formula 1]

Trehalose is a disaccharide compound and is used in cosmetics, food, pharmaceuticals and the like due to the strong moisturizing effect thereof. In addition, a substance that increases stability through hydrogen bonding with single-stranded nucleic acids is also used as a preservative for reagents containing single-stranded nucleic acids.

In an embodiment, the compound of Formula 1 was synthesized by binding two strands of oleic acid to hydrophilic trehalose, and was used as an ingredient of lipid nanoparticles stabilizing nucleic acid molecules based on hydrogen bonding.

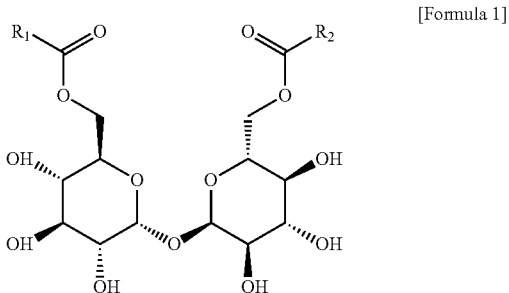

[Formula 1]

wherein $R_1$ and $R_2$ are each independently a C2-C20 saturated or unsaturated hydrocarbon.

In an embodiment, the trehalose derivative compound may include a compound represented by the following Formula 2.

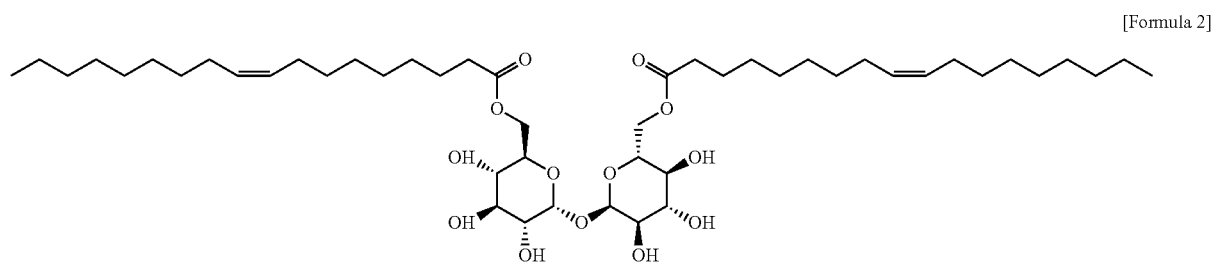 [SMILES: CCCCCCCC/C=C\CCCCCCCC(=O)OC[C@H]1O[C@H](O[C@H]2O[C@H](COC(=O)CCCCCCC/C=C\CCCCCCCC)[C@@H](O)[C@H](O)[C@H]2O)[C@H](O)[C@@H](O)[C@@H]1O]

[Formula 2]

In an embodiment of the present invention, the trehalose-based lipid compound may be present at a molar ratio of 10 to 50% with respect to the total weight of the composition.

In one aspect, the present invention provides the following lipid nanoparticle composition as a substitute compound for cholesterol, which is a component of conventional lipid nanoparticles.

In an embodiment, a lithocholic acid derivative represented by Formula 3 is provided as a first example of the cholesterol substitute for the lipid nanoparticle composition. Lithocholic acid is a type of bile acid present in the body, is suitable for replacing cholesterol in lipid nanoparticles due to the steroid structure thereof, and has positive effects on the degradation and metabolism of lipid nanoparticles after nucleic acid drug delivery because it aids in the metabolism of fatty acids.

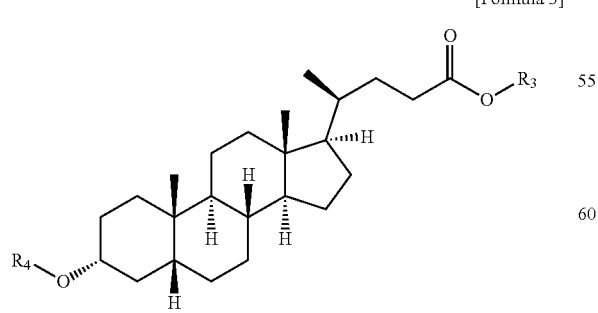

[Formula 3]

In an embodiment, in Formula 3, $R_3$ and $R_4$ include H or a C2-C20 linear or branched saturated or unsaturated hydrocarbon, and at least one of $R_3$ and $R_4$ should include a C2-C20 linear or branched saturated or unsaturated hydrocarbon.

In an embodiment, the lithocholic acid-based lipid compound may include a compound represented by the following Formulas 4 to 6:

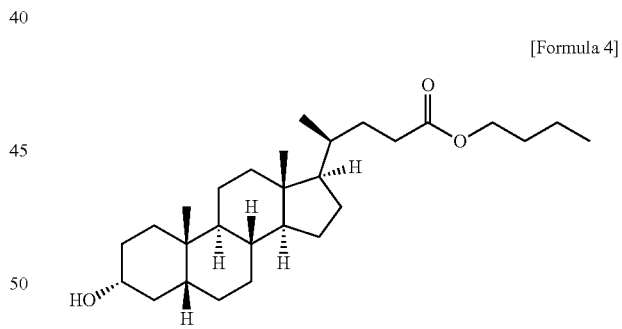

[Formula 4]

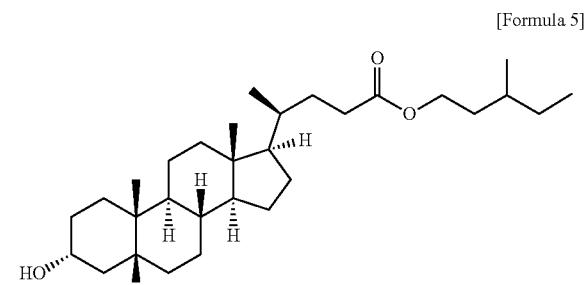

[Formula 5]

[Formula 6]

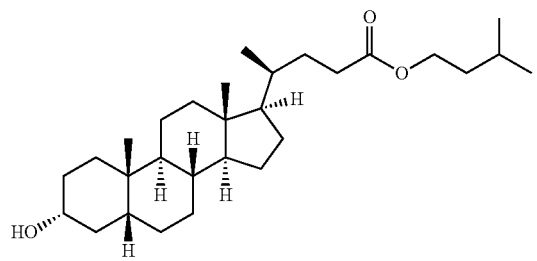

In an embodiment, a glycyrrhetinic acid derivative represented by the following Formula 7 is provided as a second example of the cholesterol substitute for the lipid nanoparticle composition. Glycyrrhetinic acid, which is a metabolite of licorice extract, is involved in the metabolic process of corticosteroids and inhibits the production of corticosteroids. Based on these actions, glycyrrhetinic acid may exhibit an anti-inflammatory effect.

[Formula 7]

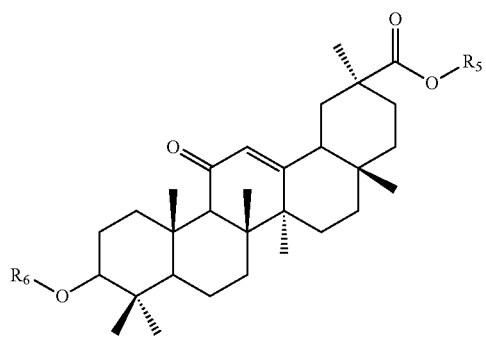

In an embodiment, in Formula 7, and $R_5$ and $R_6$ include H or a C2-C20 linear or branched saturated or unsaturated hydrocarbon, and at least one of $R_5$ and $R_6$ should include a C2-C20 linear or branched and saturated or unsaturated hydrocarbon.

In an embodiment, the glycyrrhetinic acid-based compound may include a compound represented by the following Formulas 8 to 10:

[Formula 8]

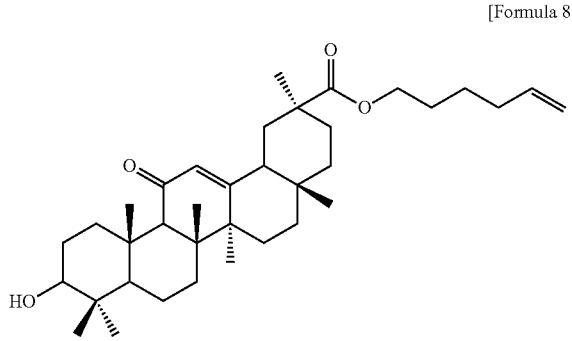

[Formula 9]

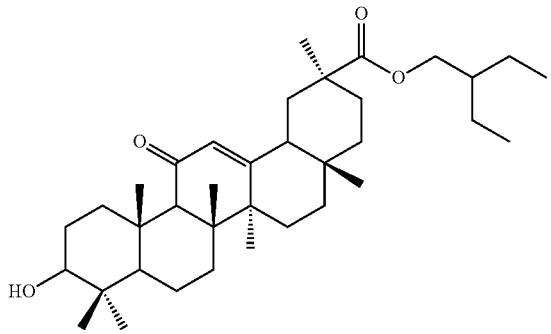

[Formula 10]

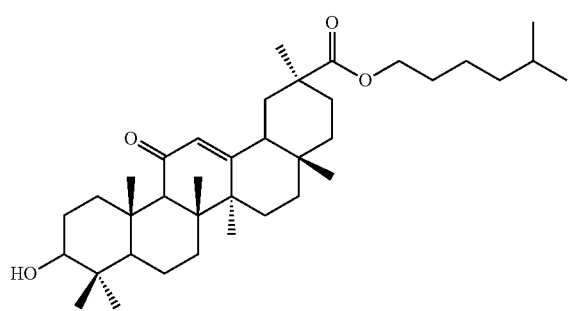

In an embodiment, a diosgenin derivative represented by Formula 11 is provided as a third example of the cholesterol substitute for the lipid nanoparticle composition. Diosgenin is a yam extract, and is a sex hormone precursor. Diosgenin is converted into DHEA in the body to produce sex hormones, and DHEA has been proven to exhibit various effects, such as memory recovery, immune function recovery, anticancer activity enhancement, heart disease prevention, and vitality enhancement.

[Formula 11]

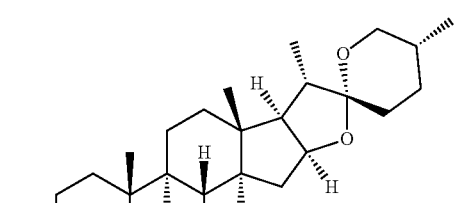

wherein $R_7$ includes —OH, —OMe, —NH$_2$, —NHMe, —NME2, —NME3, —SH, -glucose, methyl, or a saturated or unsaturated hydrocarbon having 2 to 20 carbon atoms.

In an embodiment, the diosgenin derivative compound includes at least one of the following Formulas 12 to 14:

[Formula 12]

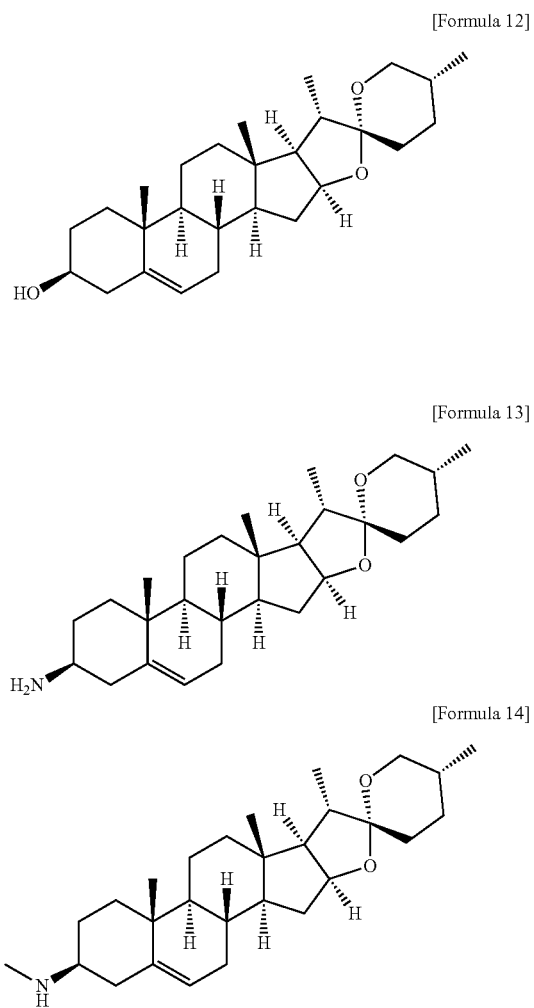

[Formula 13]

[Formula 14]

In an embodiment, the structural lipid used as a cholesterol substitute is present at a molar ratio of 20 to 50% with respect to the total nanoparticle composition.

In an embodiment, the lipid nanoparticle composition of the present invention may include an ionic lipid or an ionizable lipid. The ionic lipid herein used may be a conventional ionizable lipid having a hydrophilic head structure and a hydrophobic tail structure including nitrogen having a TNS pKa of 6 to 7, but the structure is not limited thereto. The ionizable lipid herein used may be DLin-MC3-DMA, which is an ionizable lipid for the first-generation LNP.

In an embodiment, the compound of Formula 1 is used in combination with a conventional ionizable lipid, and the total amount of Formula 1 and the conventional ionizable lipid accounts for 30 to 60% of the total weight of the composition.

In an embodiment, the lipid nanoparticle composition of the present invention may contain a phospholipid as a helper lipid. The phospholipid used herein may be DOPE (1,2-dioleoyl-sn-glycero-3-phosphoethanolamine).

In an embodiment, the lipid nanoparticle composition of the present invention may include a PEG lipid. The PEG lipid may include a PEG-conjugated lipid which is typically used to inhibit aggregation of nanoparticles, but the structure thereof is not limited thereto. The PEG lipid may be a DMG-PEG lipid.

In an embodiment, the lipid nanoparticle of the present invention is composed of five ingredients, namely the compound of Formula 1, an ionizable lipid, a phospholipid, a structure-maintaining lipid, and a PEG lipid, and more particularly, is composed of 20 to 40% of Formula 1, 20 to 40% of the ionizable lipid, 5 to 20% of the phospholipid, 30 to 60% of the structure-maintaining lipid, and 0.5 to 5% of the PEG lipid.

In an embodiment, the content and composition of the lipid nanoparticle (LNP) of the novel composition are shown in the following Table 1 described with reference to Example 5.

In an embodiment, when the lipid nanoparticle is prepared at a ratio of ionizable lipid to trehalose-based lipid to DOPE to cholesterol (or substitute compound) to DMG-PEG of 25:25:10:38.5:1.5, the lithocholic acid derivatives of Formulas 4 and 5 and retinoic acid can be used as appropriate cholesterol substitutes.

The present invention relates to a novel composition of lipid nanoparticles for stabilizing a nucleic acid drug and improving delivery in vivo, which contains a trehalose-based lipid and a compound as a cholesterol substitute.

Conventional lipid nanoparticles are composed of four compounds, namely the ionizable lipid, phospholipid, cholesterol, and PEG lipid. However, according to the present invention, it was found that when a lipid compound (Formula 2) synthesized using trehalose, which is a disaccharide compound that can interact with single-stranded nucleic acids through hydrogen bonding, is added, delivery efficiency did not remarkably decrease (LNP 93 and LNP87 in Table 1), or even increased (LNP 98 and LNP101 in Table 1), even though the amount of ionizable lipids was reduced by half compared to lipid nanoparticles not containing trehalose.

In an embodiment, when the content (molar ratio) of the trehalose-based lipid was changed from 0% (LNP101 in Table 1) to 12.5% (LNP103 in Table 1), 25% (LNP98 in Table 1), or 37.5% (LNP102 in Table 1), the delivery efficiency was changed, and when the molar ratio of ionizable lipid to trehalose-based lipid was 25%, optimal delivery efficiency was obtained.

Here, it was found that when cholesterol was substituted with lithocholic acid derivatives (Compound 4 and Compound 5) (LNP98 in Table 1), delivery efficiency was greatly increased.

Thus, the present invention provides a lipid nanoparticle for delivering a nucleic acid drug having a novel composition using ionic lipid, trehalose derivative compound, structural lipid, phospholipid and PEG lipid at a molar ratio of 1:0.70-1.30:1.30-1.80:0.35-0.45:0.03-0.09.

In an embodiment, the lipid nanoparticle contains a nucleic acid drug, which includes drugs based on nucleic acid such as mRNA for vaccines, RNA for immune boosters, siRNA, miRNA, pDNA, gene scissors, etc., and has no limitation as to length or as to whether or not a secondary structure is formed.

Hereinafter, various aspects and embodiments of the present invention will be described.

In one aspect, the present invention provided a lipid nanoparticle composition containing a lipid component, wherein the lipid nanoparticle composition contains a trehalose derivative compound represented by the following Formula 1:

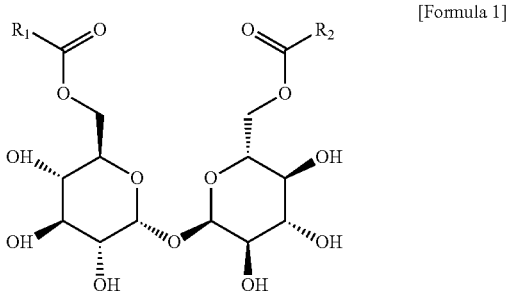

[Formula 1]

wherein $R_1$ and $R_2$ are each independently a saturated or unsaturated hydrocarbon having 2 to 20 carbon atoms.

In an embodiment, $R_1$ and $R_2$ are each independently an alkenyl group having 6 to 20 carbon atoms and including one to three unsaturated bonds.

In an embodiment, $R_1$ and $R_2$ are each independently an alkenyl group having 10 to 20 carbon atoms and including one to two unsaturated bonds.

In an embodiment, $R_1$ and $R_2$ are each independently an alkenyl group having 6 to 20 carbon atoms and including one to three unsaturated bonds.

In an embodiment, $R_1$ and $R_2$ are each independently an alkenyl group having 10 to 20 carbon atoms and including one to two unsaturated bonds.

In an embodiment, $R_1$ and $R_2$ are each independently an alkenyl group having 14 to 20 carbon atoms and including one unsaturated bond.

In an embodiment, the trehalose derivative compound is a compound represented by the following Formula 2:

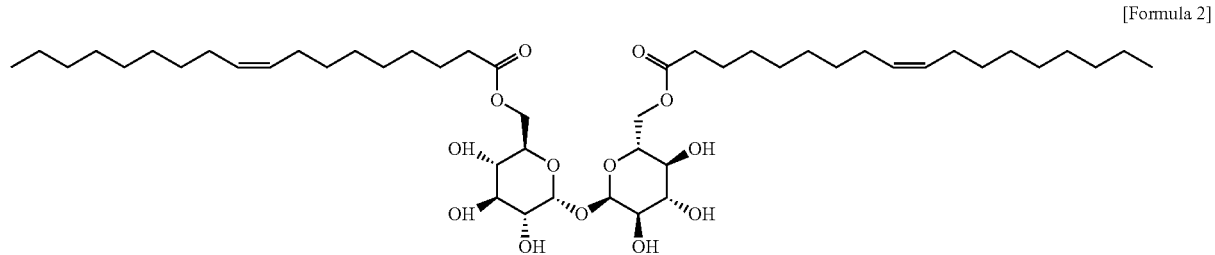 [SMILES: CCCCCCCC/C=C\CCCCCCCC(=O)OC[C@H]1O[C@H](O[C@H]2O[C@H](COC(=O)CCCCCCC/C=C\CCCCCCCC)[C@@H](O)[C@H](O)[C@H]2O)[C@H](O)[C@@H](O)[C@@H]1O]

[Formula 2]

In an embodiment, the lipid nanoparticle composition does not contain a cholesterol lipid as a structural lipid.

In an embodiment, the composition contains a lithocholic acid derivative compound represented by the following Formula 3 as a structural lipid:

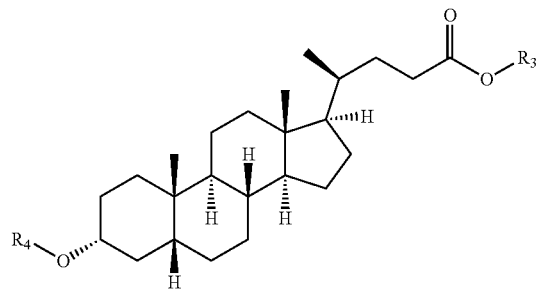

[Formula 3]

wherein $R_3$ and $R_4$ are each independently hydrogen or a saturated or unsaturated hydrocarbon having 2 to 20 carbon atoms.

In an embodiment, at least one of $R_3$ and $R_4$ is a saturated or unsaturated hydrocarbon having 2 to 20 carbon atoms.

In an embodiment, in the lithocholic acid derivative compound represented by Formula 3, $R_3$ is hydrogen and $R_4$ is an alkyl group having 3 to 7 carbon atoms.

In an embodiment, the lithocholic acid derivative compound includes at least one of the following Formulas 4 to 6:

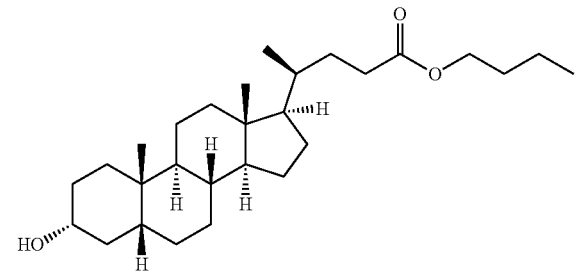

[Formula 4]

[Formula 5]

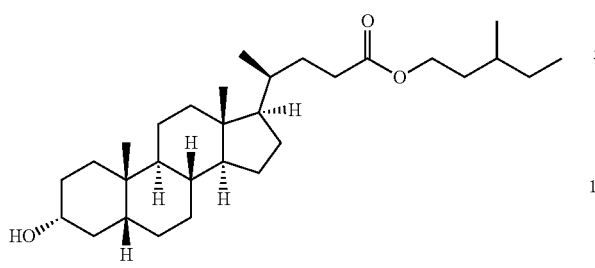

[Formula 6]

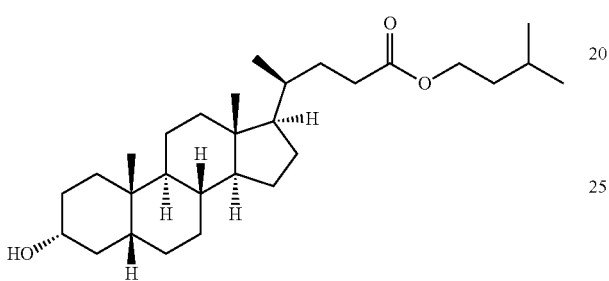

In an embodiment, the composition contains a glycyrrhetinic acid derivative compound represented by the following Formula 7 as a structural lipid:

[Formula 7]

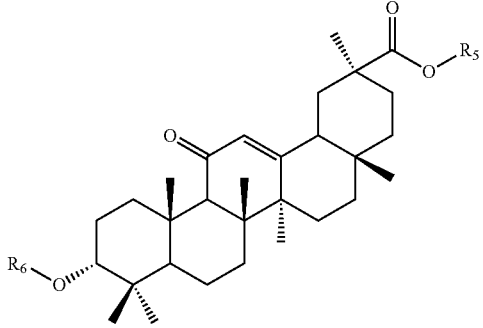

wherein $R_5$ and $R_6$ are each independently a saturated or unsaturated hydrocarbon having 2 to 20 carbon atoms.

In an embodiment, at least one of $R_5$ and $R_6$ is a saturated or unsaturated hydrocarbon having 2 to 20 carbon atoms.

In an embodiment, in the glycyrrhetinic acid derivative compound of Formula 7, $R_6$ is hydrogen and $R_5$ is an alkyl group having 3 to 8 carbon atoms or an alkenyl group having 3 to 8 carbon atoms.

In an embodiment, the glycyrrhetinic acid derivative compound includes at least one of the following Formulas 8 to 10:

[Formula 8]

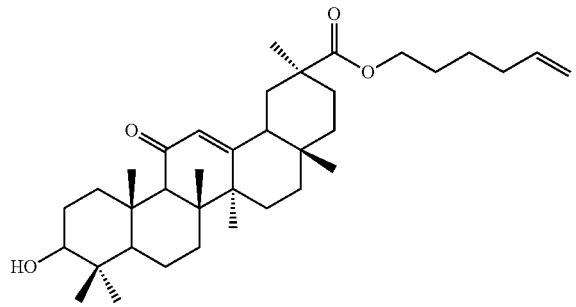

[Formula 9]

[Formula 10]

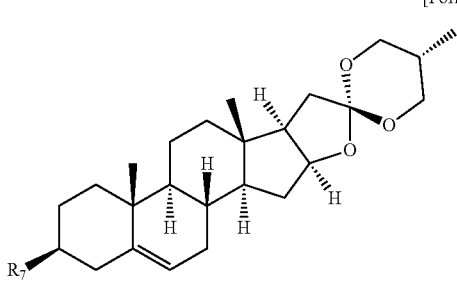

In an embodiment, the composition contains a diosgenin derivative compound represented by the following Formula 11 as a structural lipid:

[Formula 11]

wherein $R_7$ includes —OH, —OMe, —NH$_2$, —NHMe, —NME2, —NME3, —SH, -glucose, methyl, or a saturated or unsaturated hydrocarbon having 2 to 20 carbon atoms.

In an embodiment, in the diosgenin derivative compound of Formula 7, $R_6$ is a hydrogen oxide group, an amino group, or a methyl amino group.

In an embodiment, the diosgenin derivative compound includes at least one of the following Formulas 12 to 14:

[Formula 12]

[Formula 13]

[Formula 14]

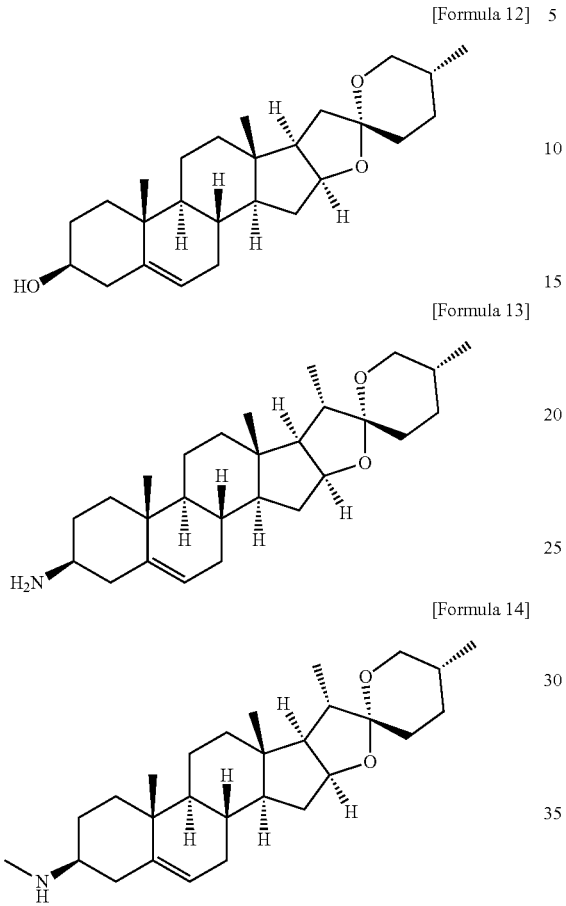

In an embodiment, the lipid nanoparticle composition contains an ionic lipid selected from the group consisting of the following compounds:

3-(didodecylamino)-N1,N1,4-tridodecyl-1-piperazineethanamine (KL10), N1-[2-(didodecylamino)ethyl]-N1,N4,N4-tridodecyl-1,4-piperazinediethanamine (KL22), 14,25-ditridecyl-15,18,21,24-tetraaza-octatriacontane (KL25), 1,2-dilinoleyloxy-N,N-dimethylaminopropane (DLin-DMA), 2,2-dilinoleyl-4-dimethylaminomethyl-[1,3]-dioxolane (DLin-K-DMA), heptatriaconta-6,9,28,31-tetraen-19-yl 4-(dimethylamino)butanoate (DLin-MC3-DMA), 2,2-dilinoleyl-4-(2-dimethylaminoethyl)-[1,3]-dioxolane (DLin-KC2-DMA), 1,2-dioleyloxy-N,N-dimethylaminopropane (DODMA), 2-({8-[(3β)-cholest-5-en-3-yloxy]octyl}oxy)-N,N-dimethyl-3-[(9Z,12Z)-octadeca-9,12-dien-1-yloxy]propan-1-amine (octyl-CLinDMA), (2R)-2-({8-[(3β)-cholest-5-en-3-yloxy]octyl}oxy)-N,N-dimethyl-3-[(9Z,12Z)-octadeca-9,12-dien-1-yloxy]propan-1-amine (octyl-CLinDMA (2R)), and (2S)-2-({8-[(3β)-cholest-5-en-3-yloxy]octyl}oxy)-N,N-dimethyl-3-[(9Z,12Z)-octadeca-9,12-dien-1-yloxy]propan-1-amine (octyl-CLinDMA (2S)).

In an embodiment, the lipid nanoparticle composition contains a phospholipid selected from the group consisting of the following compounds:

1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 diether PC), 1-oleoyl-2-cholesteryl-hemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-dioleoyl-sn-glycero-3-phosphoethanolamine (DOPE), 1,2-diphytanoyl-sn-glycero-3-phosphoethanolamine (ME 16.0 PE), 1,2-distheatoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), dipalmitoylphosphatidylglycerol (DPPG), palmitoyloleoylphosphatidylethanolamine (POPE), distearoyl-phosphatidyl-ethanolamine (DSPE), dipalmitoyl phosphatidyl ethanolamine (DPPE), dimyristoylphosphoethanolamine (DMPE), 1-stearoyl-2-oleoyl-phosphatidylethanol amine (SOPE), 1-stearoyl-2-oleoyl-phosphatidylcholine (SOPC), sphingomyelin, phosphatidylcholine, phosphatidylethanolamine, phosphatidylserine, phosphatidylinositol, phosphatidic acid, palmitoyloleoyl phosphatidylcholine, lysophosphatidylcholine, and lysophosphatidylethanolamine (LPE).

In an embodiment, the lipid nanoparticle composition further contains a PEG lipid selected from the group consisting of PEG-modified phosphatidylethanolamine, PEG-modified phosphatidic acid, PEG-modified ceramide, PEG-modified dialkylamine, PEG-modified diacylglycerol, PEG-modified dialkylglycerol, and mixtures thereof.

In an embodiment, the lipid nanoparticle composition further contains an ionic lipid, wherein the molar ratio of the ionic lipid to the trehalose derivative compound is 1:0.7 to 1:1.3.

In an embodiment, the lipid nanoparticle composition further contains a lithocholic acid derivative compound of the following Formula 3, a glycyrrhetinic acid derivative compound of the following Formula 7, or a diosgenin derivative compound represented by the following Formula 11, wherein the molar ratio of the ionic lipid to the trehalose derivative compound to the structural lipid is 1:0.70-1.30:1.30-1.80:

[Formula 3]

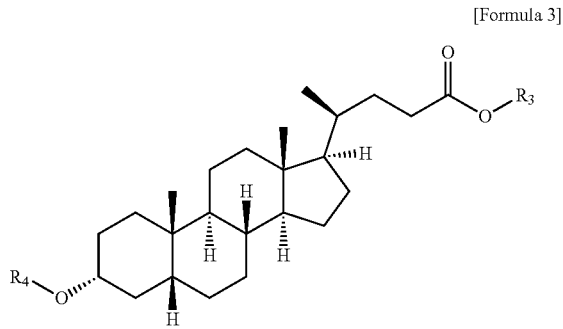

wherein $R_3$ and $R_4$ are each independently hydrogen or a saturated or unsaturated hydrocarbon having 2 to 20 carbon atoms,

[Formula 7]

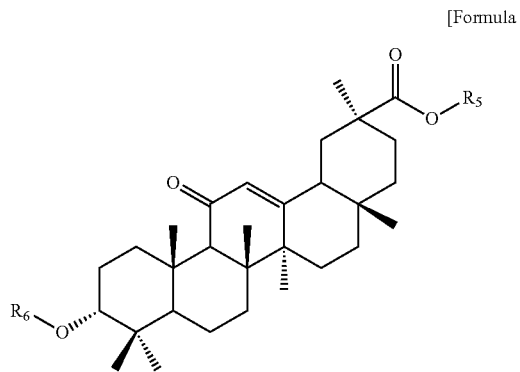

wherein $R_5$ and $R_6$ are each independently hydrogen or a saturated or unsaturated hydrocarbon having 2 to 20 carbon atoms.

[Formula 11]

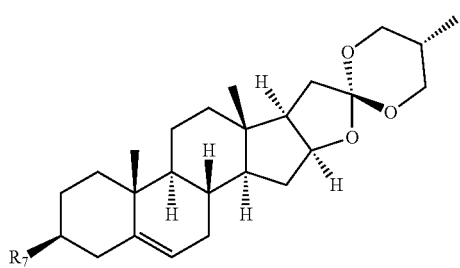

wherein $R_7$ includes —OH, —OMe, —NH$_2$, —NHMe, —NME2, —NME3, —SH, -glucose, methyl, or a saturated or unsaturated hydrocarbon having 2 to 20 carbon atoms.

In an embodiment, the lipid nanoparticle composition further contains a phospholipid, wherein the molar ratio of the ionic lipid to the trehalose derivative compound to the structural lipid to the phospholipid is 1:0.70-1.30:1.30-1.80: 0.35-0.45.

In an embodiment, the lipid nanoparticle composition further contains a PEG lipid, wherein the molar ratio of the ionic lipid to the trehalose derivative compound to the structural lipid to the phospholipid to the PEG lipid is 1:0.70-1.30:1.30-1.80:0.35-0.45:0.03-0.09.

In an embodiment, the lipid nanoparticle composition further contains an ionic lipid, a structural lipid, a phospholipid, and a PEG lipid, wherein the lipid nanoparticle composition contains 1 mol % to 59 mol %, preferably 20 mol % to 40 mol % of the ionic lipid, 1 mol % to 59 mol %, preferably 20 mol % to 40 mol %, of the trehalose derivative compound, 30 mol % to 60 mol % of the structural lipid, 5 mol % to 20 mol % of the phospholipid, and 0.5 mol % to 5 mol % of the PEG lipid.

In an embodiment, the lipid nanoparticle composition further contains a therapeutic and/or prophylactic agent.

In an embodiment, the therapeutic and/or prophylactic agent is a vaccine or compound capable of inducing an immune response.

In an embodiment, the therapeutic and/or prophylactic agent is a nucleic acid selected from the group consisting of small interfering RNA (siRNA), asymmetric interfering RNA (aiRNA), microRNA (miRNA), dicer-substrate RNA (dsRNA), small hairpin RNA (shRNA), messenger RNA (mRNA), and mixtures thereof.

In an embodiment, the encapsulation efficiency of the therapeutic and/or prophylactic agent is at least 50%.

In an embodiment, the wt/wt ratio of the lipid component to the therapeutic and/or prophylactic agent is from about 10:1 to about 60:1.

In an embodiment, the N/P ratio is from about 2:1 to about 30:1. The N/P ratio is a value obtained by dividing the number of ionizable nitrogen atoms in the ionizable lipid by the number of phosphate groups in the nucleic acid molecule.

In another aspect, the present invention provides a pharmaceutical composition containing the lipid nanoparticle composition according to one aspect of the present invention and a pharmaceutically acceptable carrier.

In another aspect, the present invention provides a method of delivering a therapeutic and/or prophylactic agent to mammalian cells, the method including administering to a subject the lipid nanoparticle composition according to one aspect of the present invention, wherein the administration includes bringing the mammalian cells into contact with the nanoparticle composition to deliver the therapeutic and/or prophylactic agent to the mammalian cells.

In an embodiment, the mammalian cells are derived from a mammal.

In an embodiment, the mammal is a human.

In an embodiment, the nanoparticle composition may be administered intravenously, intramuscularly, intradermally, subcutaneously, intranasally, or by inhalation.

In an embodiment, the therapeutic and/or prophylactic agent is administered at a dose of about 0.01 mg/kg to about 10 mg/kg to the mammal.

In another aspect, the present invention provides a method for producing a polypeptide of interest in mammalian cells, the method including bringing the cells into contact with the lipid nanoparticle composition of the present invention, wherein the therapeutic and/or prophylactic agent is mRNA, wherein the mRNA encodes the polypeptide of interest so that the mRNA can be translated in cells to produce the polypeptide of interest.

Hereinafter, the present invention will be described in more detail with reference to specific examples. However, the following examples are provided only for better understanding of the present invention, and thus should not be construed as limiting the scope of the present invention.

Example 1: Synthesis of Trehalose-Based Lipids

Trehalose dihydrate (200 mg, 0.53 mmol) was dissolved in pyridine (5 mL), sequentially added with TBTU (421 mg, 1.3 mmol), DIPEA (320 µL, 1.2 mmol), and oleic acid (370 µL, 1.2 mmol), and charged with argon gas, after which the resulting mixture was stirred at room temperature for 20 hours. The solvent was removed using a rotary vacuum distiller, and the residue was primarily purified by column chromatography and then dried (SiO$_2$, 2:98→10:90 MeOH/EtOAc).

The dried solid was washed several times with EtOAc and then completely dried to obtain 287 mg (62%) of the compound of Formula 2.

$^1$H NMR (400 MHz, MeOD) δ 5.38 (t, 4H, J=4.5 Hz), 5.08 (d, 2H, J=3.8 Hz), 4.39 (dd, 2H, J=11.9, 2.2 Hz), 4.23

(dd, 2H, J=11.9, 5.1 Hz), 4.04 (ddd, 2H, J=10.2, 5.3, 2.1 Hz), 3.81 (dd, 2H, J=9.6, 9.4 Hz), 3.50 (dd, 2H, J=9.6, 3.6 Hz), 3.35 (dd, 2H, J=10.0, 8.8 Hz), 2.042.09 (m, 8H), 2.37 (t, 4H, J=7.4 Hz), 1.611.67 (m, 4H), 1.291.41 (m, 40H), 0.93 (t, 6H, J=6.8 Hz).

$^{13}$C NMR (100 MHz, MeOD) δ 174.0, 129.5, 129.4, 93.8, 73.2, 71.8, 70.5, 70.1, 63.0, 33.7, 31.7, 29.5, 29.4, 29.2, 29.1, 29.0, 28.9, 28.8, 28.8, 26.8, 24.7, 22.4, 13.1.

Example 2: Synthesis of Lithocholic Acid Derivatives

Lithocholic acid and the corresponding alcohol were placed in a reaction vessel, an HCl solution (35-37% aqueous solution, 1 equivalent) was added thereto, and the mixture was stirred at room temperature for 24 hours. The alcohol was distilled using a rotary vacuum distiller, the residue was dissolved again in DCM, and the impurities were extracted with a NaHCO$_3$ saturated aqueous solution and then a saturated brine. Then, the DCM layer was dehydrated with anhydrous Na$_2$SO$_4$ to remove moisture, the residue was filtered out, and the filtrate was dried using a rotary vacuum distiller and purified by column chromatography (SiO$_2$, 19:1 to 49:1 DCM/MeOH).

As a result, the lithocholic acid derivative compounds of Formula 4 (92%), Formula 5 (87%) and Formula 6 (79%) were obtained.

Formula 4: MS (FAB-MS) calcd. for C$_{28}$H$_{49}$O$_3$ [M−H]$^-$ 431.4, found 431.2; calcd. for C$_{28}$H$_{47}$O$_2$ [M−OH]$^+$ 415.4, found 415.2.

Formula 5: MS (ESI-MS) calcd. for C$_{30}$H$_{51}$O$_3$ [M−H]$^-$ 459.4, found 459.3; calcd. for C$_{30}$H$_{51}$O$_2$ [M−OH]$^-$ 443.4, found 443.3.

Formula 6: MS (ESI-MS) calcd. for C$_{29}$H$_{49}$O$_3$ [M−H]$^-$ 445.4, found 445.2; calcd. for C$_{29}$H$_{44}$O$_2$ [M−OH]$^-$ 429.4, found 429.

Example 3: Synthesis of Glycyrrhetinic Acid Derivatives

Glycyrrhetinic acid was dissolved in DMF, K$_2$CO$_3$ (1.5 equivalents) was added thereto, the mixture was stirred at room temperature for 30 minutes, the corresponding alkyl bromide (1.2 equivalents) was added thereto, and the mixture was again stirred at room temperature in the presence of argon gas for 24 hours. The DMF was removed using a rotary vacuum distiller and was dissolved again in DCM and charged in a separatory funnel, impurities were extracted with a 0.5N HCl aqueous solution and saturated brine, and the DCM layer was dehydrated with anhydrous Na$_2$SO$_4$ and filtered. The filtrate was dried using a rotary vacuum distiller and purified through column chromatography (SiO$_2$, 4:1~9:1 hexane/EtOAc).

As a result, the glycyrrhetinic acid derivative compounds of Formula 8 (97%), Formula 9 (96%), and Formula 10 (99%) were obtained.

Formula 8: MS (FAB-HRMS) calcd. for C$_{36}$H$_{57}$O$_4$ [M+H]$^+$ 553.4257, found 553.4259.

Formula 9: MS (FAB-HRMS) calcd. for C$_{36}$H$_{59}$O$_4$ [M+H]$^+$ 555.4413, found 555.4410.

Formula 10: MS (FAB-HRMS) calcd. for C$_{37}$H$_{51}$O$_4$ [M+H]$^+$ 569.4570, found 569.4573.

Example 4: Synthesis of Diosgenin Derivatives

[Step 1] Formula 12 (diosgenin, 0.50 g, 1.2 mmol), TsOCl (1.1 g, 5.5 mmol), anhydrous pyridine (0.95 mL, 11 mmol) and a small amount of DMAP were dissolved in anhydrous DCM in a reaction vessel and then stirred at 0° C. for 24 hours. After completion of the reaction, the organic reaction solution was washed sequentially with 5% HCl aqueous solution and saturated Na$_2$HCO$_3$ aqueous solution, and the DCM layer was dried over anhydrous MgSO$_4$ and concentrated without further purification.

[Step 2] The concentrate obtained in step 1 was dissolved in anhydrous DMF along with NaN$_3$ (0.95 g, 15 mmol) under an atmosphere of argon gas and stirred at 60° C. for 22 hours. After completion of the reaction, the reaction solution was diluted with EtOAc and washed with saturated brine. The organic layer was dried over anhydrous MgSO$_4$, filtered, concentrated, and separated by column chromatography (SiO$_2$, petroleum ether/EtOAc, 150:1 volume ratio) to obtain an intermediate product at a yield of 36%.

[Step 3] The intermediate product obtained in step 2 and PPhs (0.99 g, 3.8 mmol) were dissolved in a mixed solvent of THF/distilled water (10:1 volume ratio) under an atmosphere of argon gas, followed by stirring at 60° C. for 7 hours. After completion of the reaction, the reaction mixture was concentrated and separated by column chromatography (SiO$_2$, DCM/MeOH, 50:1 volume ratio) to obtain Formula 13 (85%) as a white solid.

$^1$H NMR (400 MHz, CDCl$_3$) δ 5.34 (d, J=5.1 Hz, 1H), 4.60 (d, J=7.9 Hz, 1H), 4.44-4.34 (m, 1H), 3.87-3.80 (m, 1H), 3.45 (ddd, J=11.0, 4.5, 2.0 Hz, 1H), 3.35 (t, J=10.9 Hz, 1H), 2.54 (d, J=14.7 Hz, 1H), 1.42 (s, 9H).

$^{13}$C NMR (100 MHz, CDCl$_3$) δ 155.18, 139.05, 123.12, 109.37, 80.89, 79.06, 66.94, 62.21, 56.64, 50.36, 46.72, 41.71, 40.34, 39.88, 37.53, 37.43, 34.00, 32.16, 31.92, 31.49, 31.44, 30.40, 28.91, 28.57, 26.49, 20.65, 18.99, 17.25, 16.37, 14.63.

Formula 13 (261 mg, 0.61 mmol), Et3N (94 µL, 0.67 mmol), and BOC$_2$O (147 mg, 0.67 mmol) were dissolved in anhydrous DCM under an atmosphere of argon gas and stirred at room temperature for 20 hours. After completion of the reaction, the resulting reaction was further diluted with DCM and then washed sequentially with distilled water and saturated brine. The organic layer was dried over anhydrous sodium sulfate and filtered, and then the resulting concentrate was separated by column chromatography (SiO$_2$, 16:1 hexane/EtOAc) to obtain the compound of Formula 14 (quantitative) as a white solid.

$^1$H NMR (400 MHz, CDCl$_3$) δ 5.34 (dd, J=4.4, 2.6 Hz, 1H), 4.39 (td, J=7.9, 6.4 Hz, 1H), 3.46 (ddd, J=10.9, 4.4, 2.0 Hz, 1H), 3.36 (t, J=10.9 Hz, 1H), 2.78 (t, J=3.3 Hz, 1H), 2.47 (dq, J=14.4, 3.0 Hz, 1H), 2.36 (s, 3H).

$^{13}$C NMR (100 MHz, CDCl$_3$) δ 139.30, 122.75, 109.38, 80.95, 66.96, 62.22, 56.63, 54.89, 50.23, 41.74, 40.37, 39.90, 37.55, 36.70, 33.49, 33.22, 32.15, 31.95, 31.53, 30.44, 29.83, 28.95, 25.19, 20.69, 19.26, 17.27, 16.40, 14.65.

MS (ESI-MS) calcd. for C$_{26}$H$_{46}$NO$_2$ [M+H]$^+$ 428.3523, found 428.3525.

Example 5: Construction of Nucleic Acid Molecules of RNA Platform

An RNA platform in which a nucleic acid sequence encoding Renilla luciferase (R/L), which has an IRES element derived from encephalomyocarditis virus (EMCV) and is a known reporter gene, was inserted as a target sequence was constructed. The template DNA was designed and the nucleic acid molecule of the single-stranded RNA platform was constructed using an IVT procedure.

Example 6: Preparation of Lipid Nanoparticles

Lipid nanoparticles were prepared from 0.625 mg/mL of an RNA solution (50 mM sodium citrate buffer, 110 mM NaCl, pH=4.0) and a lipid-mixture solution (ethanol) using a laboratory mixer and emulsifier (NanoAssembir Spark, Precision NanoSystems) and subjected to solvent conversion with physiological saline using a filter tube for centrifugation (UFC5010, Amicon).

Specifically, the content was prepared as shown in Table 1 below.

TABLE 1

| Names | Ionizable lipid (molar ratio) | Additional component (molar ratio) | Structural lipid (molar ratio) | Phospholipid (molar ratio) | PEG-lipid (molar ratio) |
|---|---|---|---|---|---|
| LNP87 | DLin-MC3-DMA(50) | — | cholesterol (38.5) | DOPE (10) | DMG-PEG (1.5) |
| LNP93 | DLin-MC3-DMA(25) | Formula 2 (25) | cholesterol (38.5) | DOPE (10) | DMG-PEG (1.5) |
| LNP98 | DLin-MC3-DMA(25) | Formula 2 (25) | Formula 4 (38.5) | DOPE (10) | DMG-PEG (1.5) |
| LNP100 | — | Formula 2 (50) | Formula 4 (38.5) | DOPE (10) | DMG-PEG (1.5) |
| LNP101 | DLin-MC3-DMA(50) | — | Formula 4 (38.5) | DOPE (10) | DMG-PEG (1.5) |
| LNP102 | DLin-MC3-DMA(12.5) | Formula 2 (37.5) | Formula 4 (38.5) | DOPE (10) | DMG-PEG (1.5) |
| LNP103 | DLin-MC3-DMA(37.5) | Formula 2 (12.5) | Formula 4 (38.5) | DOPE (10) | DMG-PEG (1.5) |
| LNP105 | DLin-MC3-DMA(25) | Formula 2 (25) | Formula 8 (38.5) | DOPE (10) | DMG-PEG (1.5) |
| LNP106 | DLin-MC3-DMA(25) | Formula 2 (25) | Formula 9 (38.5) | DOPE (10) | DMG-PEG (1.5) |
| LNP107 | DLin-MC3-DMA(25) | Formula 2 (25) | Formula 10 (38.5) | DOPE (10) | DMG-PEG (1.5) |
| LNP112 | DLin-MC3-DMA(25) | Formula 2 (25) | Formula 5 (38.5) | DOPE (10) | DMG-PEG (1.5) |
| LNP113 | DLin-MC3-DMA(25) | Formula 2 (25) | Formula 6 (38.5) | DOPE (10) | DMG-PEG (1.5) |
| LNP154 | DLin-MC3-DMA(25) | Formula 2 (25) | Formula 12 (38.5) | DOPE (10) | DMG-PEG (1.5) |
| LNP156 | DLin-MC3-DMA(25) | Formula 2 (25) | Formula 13 (38.5) | DOPE (10) | DMG-PEG (1.5) |
| LNP158 | DLin-MC3-DMA(25) | Formula 2 (25) | Formula 14 (38.5) | DOPE (10) | DMG-PEG (1.5) |

In an embodiment, it was found that when lipid nanoparticles were prepared from an ionizable lipid, trehalose-based lipid, DOPE, cholesterol (or substitute compound), and DMG-PEG at a ratio of 25:25:10:38.5:1.5, the lithocholic acid derivatives of Formulas 4 and 5 and retinoic acid can be used as appropriate cholesterol substitutes.

Experimental Example 1: Evaluation of Delivery Efficiency by Detection Of Protein Expression Level mRNA-LNP was intradermally injected into the ears of ICR mice at an RNA standard of 5 ug/20 µl and expression was confirmed.

The experiment was performed according to the following procedure. Each experimental group was prepared at a dose of 5 ug/20 µl of RNA and was intradermally injected into the ear of each mouse. Then, expression was identified based on the maximum expression time of the target protein. R/L, which was actually tested, expression, and maintenance were detected at two points of time: after 6 hours and 24 hours.

The specific experimental procedure was as follows.

Each mouse was anesthetized using a respiratory anesthetic, and a drug that satisfied the experimental conditions was injected into the mouse through an insulin syringe. Then, each mouse was anesthetized using $CO_2$ at the corresponding time and the ear was cut from the mouse. The cut ear was immersed in 300 µl of 1× Renilla lysis buffer and completely pulverized using scissors and a homogenizer. Then, 20 µl of the mixture was transferred to a white 96-well plate, 100 µl of Renilla luciferase assay substrate from Promega Corporation was added thereto, and luminescence was measured to compare expression.

The experimental results were as follows.

FIG. 1 illustrates the protein expression efficiency of lipid nanoparticles (LNP 87, 93, 98, 100) of a novel composition containing Renilla luciferase (R/L) mRNA, determined based on the amount of Renilla luciferase (R/L) expressed 6 hours and 24 hours after injection into the ears of mice.

Figure 2:
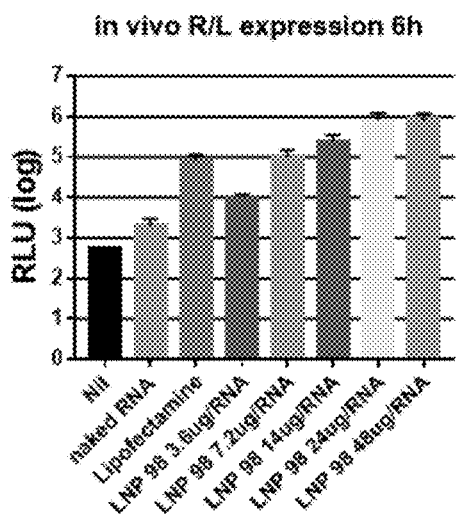
FIG. 2 illustrates the result of analysis of an optimal RNA/lipid ratio from the expression level of R/L using 3.6, 7.2, 12, 24, and 48 μg of lipids compared to 1 μg of R/L mRNA with respect to LNP No. 98.
Figure 2:
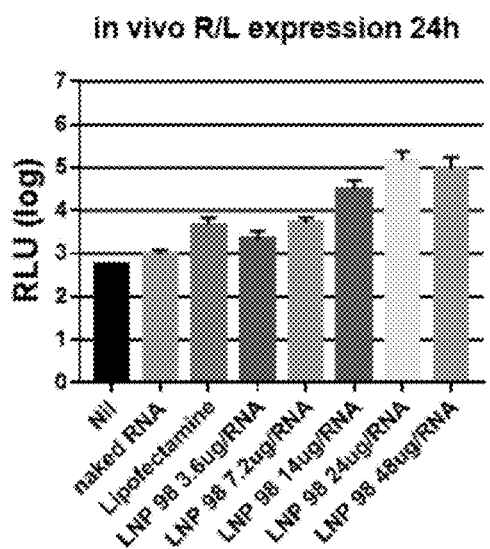

FIG. 2 illustrates the result of analysis of an optimal RNA/lipid ratio from the expression level of R/L using 3.6, 7.2, 12, 24, and 48 µg of lipids compared to 1 µg of R/L mRNA with respect to LNP No. 98.

Figure 3:
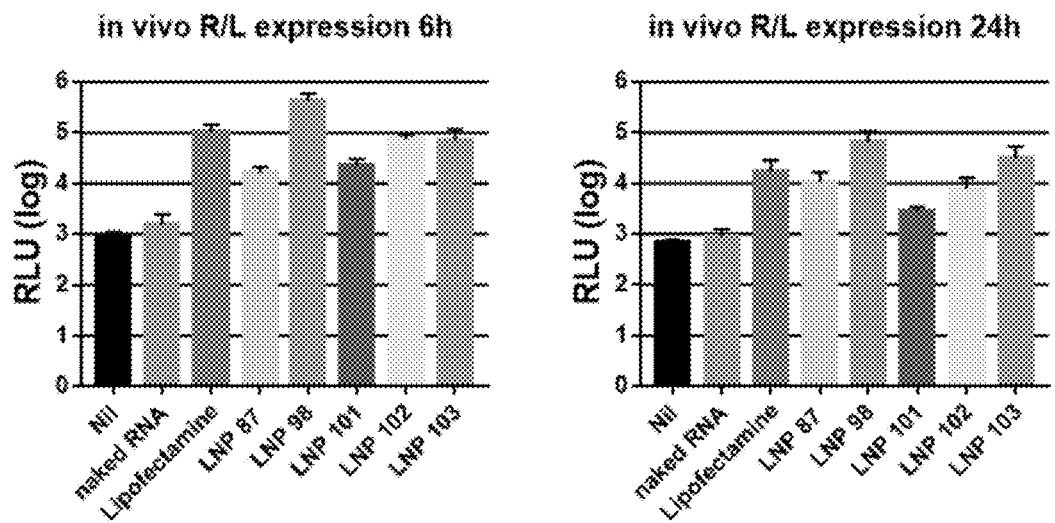
FIG. 3 illustrates the result of analysis of R/L mRNA delivery efficiency depending on the trehalose content based on the R/L expression level.

FIG. 3 illustrates the result of analysis of R/L mRNA delivery efficiency depending on the trehalose content based on the R/L expression level.

Figure 4:
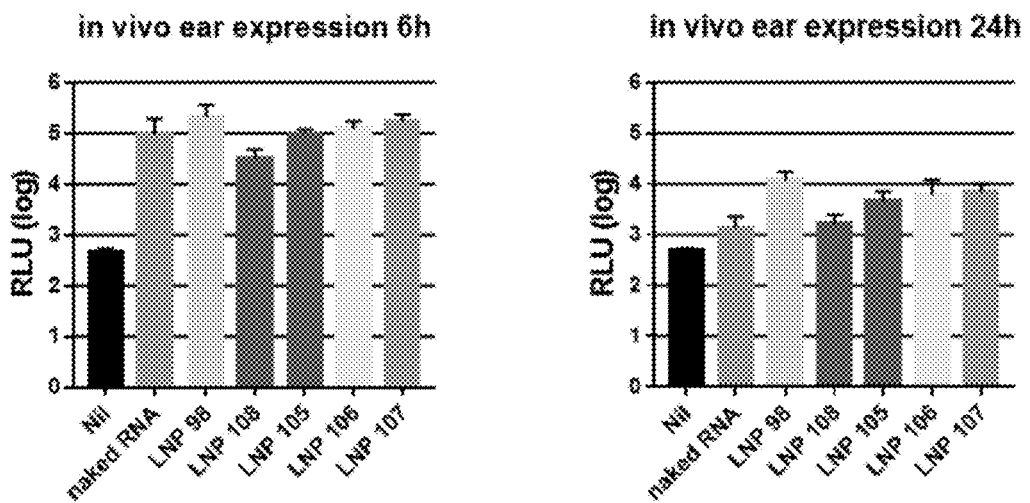
FIGS. 4 to 6 illustrate the results of analysis of R/L mRNA delivery efficiency based on the R/L expression level depending on the type of compound that is used as a cholesterol substitute.
Figure 5:
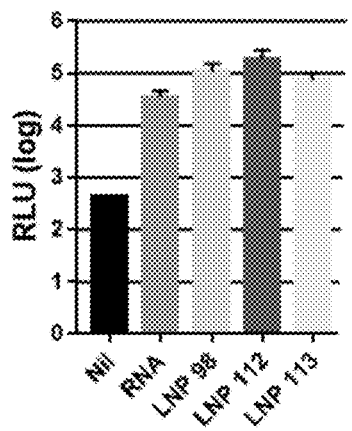
Figure 5:
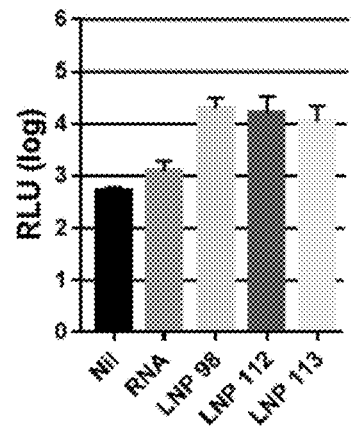
Figure 6:
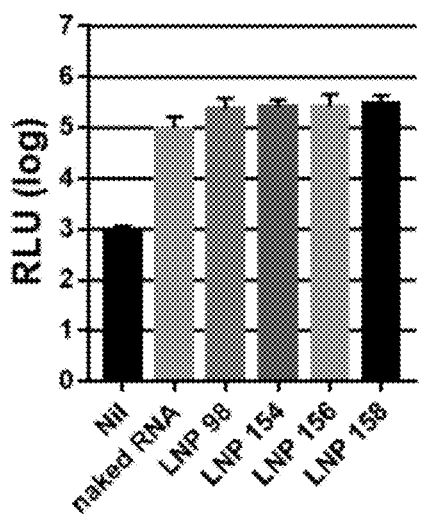
Figure 6:
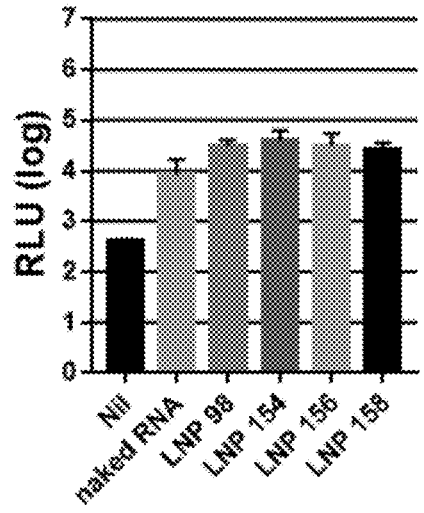
Figure 7:
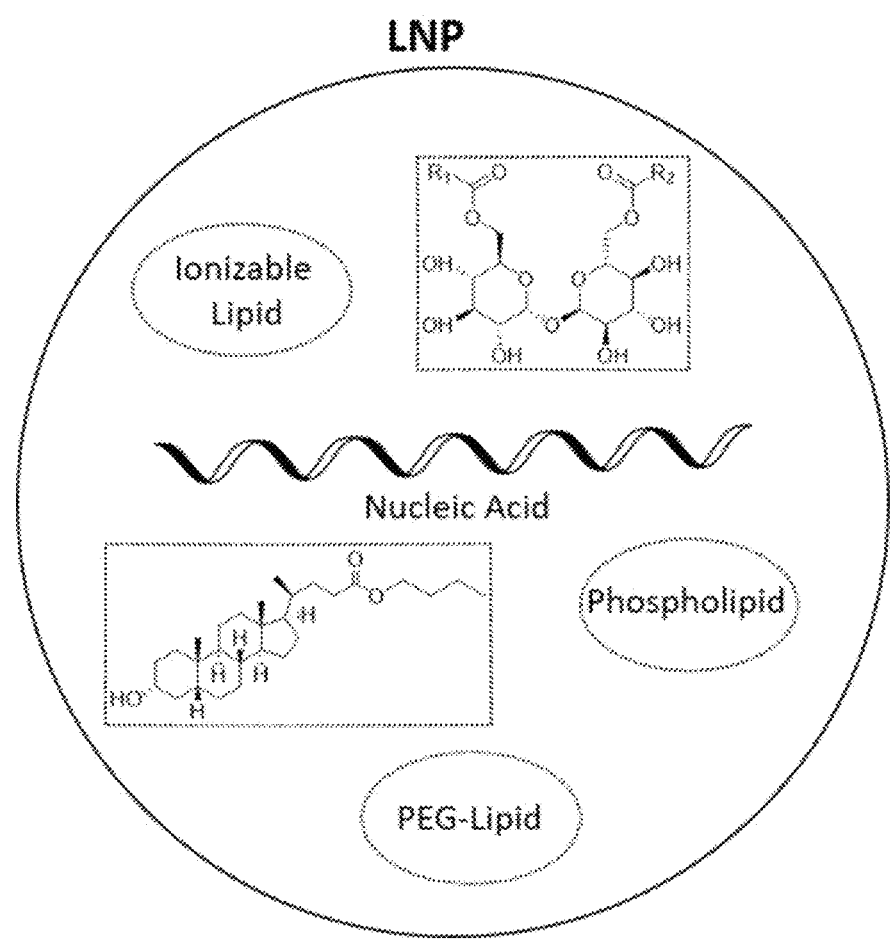
FIG. 7 is a conceptual diagram illustrating the components of the lipid nanoparticle composition of one embodiment of the present invention.

FIGS. 4 to 6 illustrate the results of analysis of R/L mRNA delivery efficiency depending on the type of compound substituted for cholesterol based on the R/L expression level.

Conventional lipid nanoparticles are composed of four compounds: an ionizable lipid, phospholipid, cholesterol, and PEG-lipid. However, in the present invention, it was found that when lipid compounds synthesized using trehalose, which is a disaccharide compound capable of interacting with single-stranded nucleic acids by hydrogen bonding, were added (Formula 2), the delivery efficiency was not greatly reduced (LNP 93 and LNP87 in Table 1), or increased (LNP 98 and LNP101 in Table 1), even though the amount of ionizable lipid was half that of lipid nanoparticles not containing trehalose.

In an embodiment, when the content (molar ratio) of the trehalose-based lipid was changed from 0% (LNP101 in Table 1) to 12.5% (LNP103 in Table 1), 25% (LNP98 in Table 1), or 37.5% (LNP102 in Table 1), the delivery efficiency was changed, and when the molar ratio of ionizable lipid to trehalose-based lipid was 25%, optimal delivery efficiency was obtained.

Here, it was found that when cholesterol was substituted with lithocholic acid derivatives (Compound 4 and Compound 5) (LNP98 in Table 1), the delivery efficiency was remarkably increased.

The lipid nanoparticles according to one aspect of the present invention can stabilize nucleic acid drugs and improve delivery in vivo compared to conventional lipid nanoparticles.

Considering the expression efficiency of the mRNA-encoded protein in vivo using the lipid nanoparticles produced according to the present invention, lipid nanoparticles appropriately containing a trehalose-based lipid exhibited improved expression efficiency compared to that of lipid nanoparticles not containing the trehalose-based lipid.

According to one aspect of the present invention, the optimal ratio of the trehalose-based lipid to the ionizable lipid was a 1:1 molar ratio, the optimal ratio of RNA to lipid was 1:24 in terms of weight ratio, and the N/P ratio was 3 (N/P ratio: the value obtained by dividing the number of ionizable nitrogen atoms in the ionizable lipid by the number of phosphate groups in the nucleic acid molecule).

In addition, when a cholesterol substitute is used for the lipid nanoparticles according to one aspect of the present invention, better effects can be obtained than when conventional cholesterol is used.

The effects of the present invention are not limited to those mentioned above. It should be understood that the effects of the present invention include all effects that can be inferred from the description of the present invention.

The present invention has been described in detail with reference to embodiments thereof. However, it will be appreciated by those skilled in the art that changes may be made in the embodiments without departing from the principles and spirit of the present invention, the scope of which is defined in the appended claims and equivalents thereto.

What is claimed is:

1. A lipid nanoparticle composition comprising a lipid component,
wherein the lipid nanoparticle composition comprises:
a trehalose derivative compound represented by the following Formula 1; and
a lithocholic acid derivative compound represented by the following Formula 3 as a structural lipid:

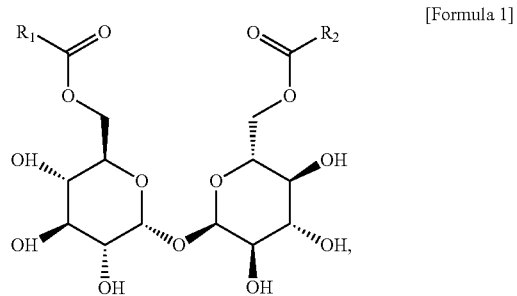

[Formula 1]

wherein $R_1$ and $R_2$ are each independently an unsaturated hydrocarbon having 2 to 20 carbon atoms,

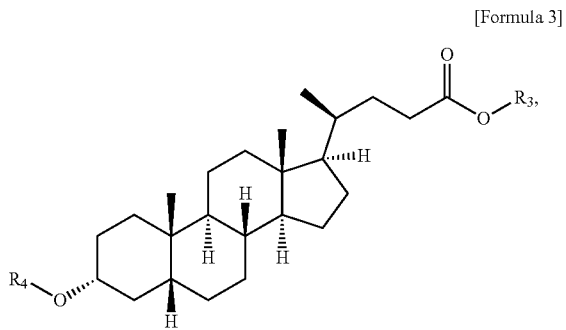

[Formula 3]

wherein at least one of R3 and R4 is a saturated or unsaturated hydrocarbon having 2 to 20 carbon atoms.

2. The lipid nanoparticle composition according to claim 1, wherein $R_1$ and $R_2$ are each independently an alkenyl group having 6 to 20 carbon atoms and including 1 to 3 unsaturated bonds.

3. The lipid nanoparticle composition according to claim 1, wherein the trehalose derivative compound is a compound represented by the following Formula 2:

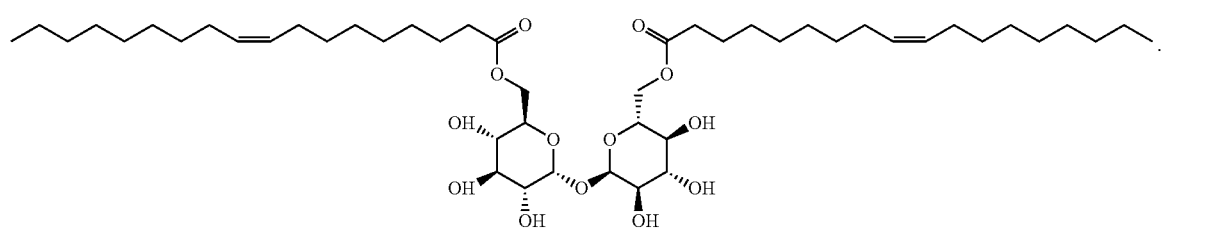

[Formula 2]

4. The lipid nanoparticle composition according to claim 1, wherein the lipid nanoparticle composition does not comprise a cholesterol lipid as a structural lipid.

5. The lipid nanoparticle composition according to claim 4, wherein the lithocholic acid derivative compound comprises at least one of the following Formulas 4 to 6:

[Formula 4]

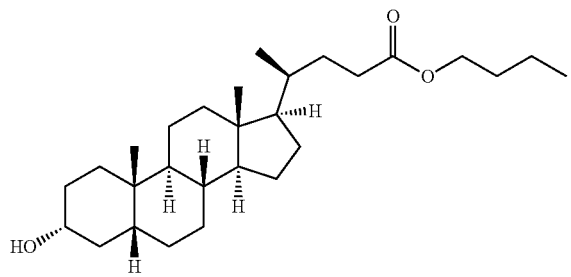

[Formula 5]

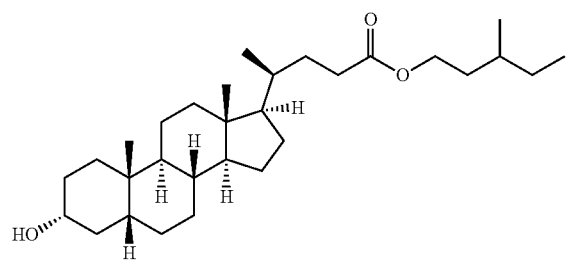

[Formula 6]

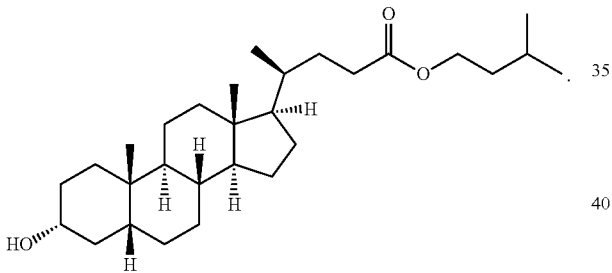

6. The lipid nanoparticle composition according to claim 4, wherein the lipid nanoparticle composition further comprises a glycyrrhetinic acid derivative compound represented by the following Formula 7 as a structural lipid:

[Formula 7]

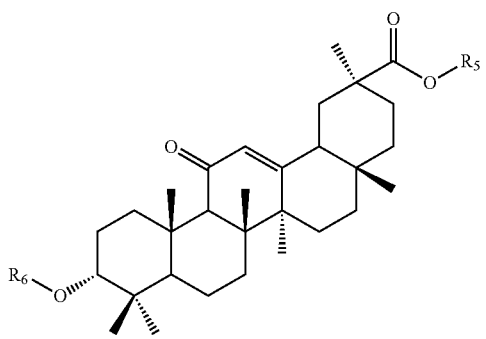

wherein $R_5$ and $R_6$ are each independently a saturated or unsaturated hydrocarbon having 2 to 20 carbon atoms.

7. The lipid nanoparticle composition according to claim 6, wherein at least one of $R_5$ and $R_6$ is a saturated or unsaturated hydrocarbon having 2 to 20 carbon atoms.

8. The lipid nanoparticle composition according to claim 4, wherein the lipid nanoparticle composition further comprises a diosgenin derivative compound represented by the following Formula 11 as a structural lipid:

[Formula 11]

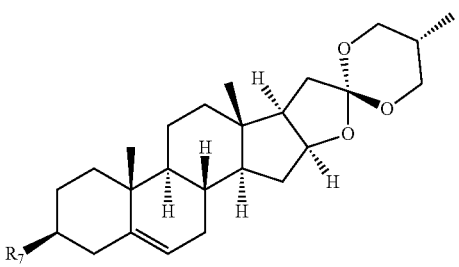

wherein $R_7$ includes —OH, —OMe, —NH$_2$, —NHMe, —NME2, —NME3, —SH, -glucose, methyl, or a saturated or unsaturated hydrocarbon having 2 to 20 carbon atoms.

9. The lipid nanoparticle composition according to claim 8, wherein the diosgenin derivative compound comprises at least one of the following Formulas 12 to 14:

[Formula 12]

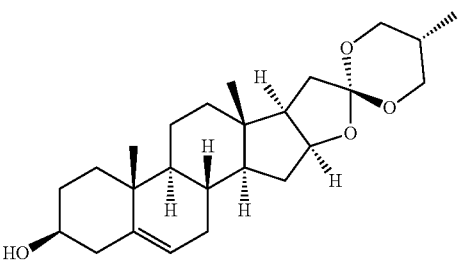

[Formula 13]

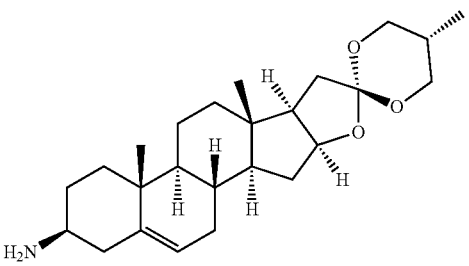

[Formula 14]

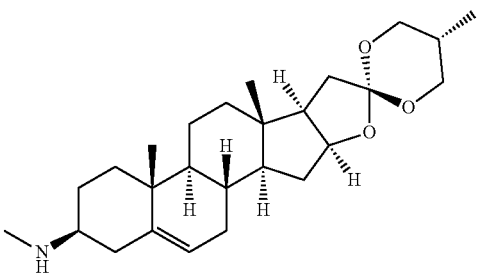

10. The lipid nanoparticle composition according to claim 1, wherein the lipid nanoparticle composition further comprises an ionic lipid selected from the group consisting of the following compounds:
- 3-(didodecylamino)-N1,N1,4-tridodecyl-1-piperazineethanamine (KL10),
- N1-[2-(didodecylamino)ethyl]-N1,N4,N4-tridodecyl-1,4-piperazinediethanamine (KL22),
- 14,25-ditridecyl-15,18,21,24-tetraaza-octatriacontane (KL25),
- 1,2-dilinoleyloxy-N,N-dimethylaminopropane (DLin-DMA),
- 2,2-dilinoleyl-4-dimethylaminomethyl-[1,3]-dioxolane (DLin-K-DMA),
- heptatriaconta-6,9,28,31-tetraen-19-yl 4-(dimethylamino) butanoate (DLin-MC3-DMA),
- 2,2-dilinoleyl-4-(2-dimethylaminoethyl)-[1,3]-dioxolane (DLin-KC2-DMA),
- 1,2-dioleyloxy-N,N-dimethylaminopropane (DODMA),
- 2-({8-[(3β)-cholest-5-en-3-yloxy]octyl}oxy)-N,N-dimethyl-3-[(9Z,12Z)-octadeca-9,12-dien-1-yloxy]propan-1-amine (octyl-CLinDMA),
- (2R)-2-({8-[(3β)-cholest-5-en-3-yloxy]octyl}oxy)-N,N-dimethyl-3-[(9Z,12Z)-octadeca-9,12-dien-1-yloxy]propan-1-amine (octyl-CLinDMA (2R)), and
- (2S)-2-({8-[(3β)-cholest-5-en-3-yloxy]octyl}oxy)-N,N-dimethyl-3-[(9Z,12Z)-octadeca-9,12-dien-1-yloxy]propan-1-amine (octyl-CLinDMA (2S)).

11. The lipid nanoparticle composition according to claim 1, wherein the lipid nanoparticle composition further comprises a phospholipid selected from the group consisting of the following compounds:
- 1,2-dilinoleoyl-sn-glycero-3-phosphocholine (DLPC),
- 1,2-dimyristoyl-sn-glycero-phosphocholine (DMPC),
- 1,2-dioleoyl-sn-glycero-3-phosphocholine (DOPC),
- 1,2-dipalmitoyl-sn-glycero-3-phosphocholine (DPPC),
- 1,2-distearoyl-sn-glycero-3-phosphocholine (DSPC),
- 1,2-diundecanoyl-sn-glycero-phosphocholine (DUPC),
- 1-palmitoyl-2-oleoyl-sn-glycero-3-phosphocholine (POPC),
- 1,2-di-O-octadecenyl-sn-glycero-3-phosphocholine (18:0 diether PC),
- 1-oleoyl-2-cholesterylhemisuccinoyl-sn-glycero-3-phosphocholine (OChemsPC),
- 1-hexadecyl-sn-glycero-3-phosphocholine ($C_{16}$ Lyso PC),
- 1,2-dilinolenoyl-sn-glycero-3-phosphocholine,
- 1,2-diarachidonoyl-sn-glycero-3-phosphocholine,
- 1,2-didocosahexaenoyl-sn-glycero-3-phosphocholine,
- 1,2-dioleoyl-sn-glycero-3-phosphoethanolamine (DOPE),
- 1,2-diphytanoyl-sn-glycero-3-phosphoethanolamine (ME 16.0 PE),
- 1,2-disthearoyl-sn-glycero-3-phosphoethanolamine,
- 1,2-dilinoleoyl-sn-glycero-3-phosphoethanolamine,
- 1,2-dilinolenoyl-sn-glycero-3-phosphoethanolamine,
- 1,2-diarachidonoyl-sn-glycero-3-phosphoethanolamine,
- 1,2-didocosahexaenoyl-sn-glycero-3-phosphoethanolamine,
- 1,2-dioleoyl-sn-glycero-3-phospho-rac-(1-glycerol) sodium salt (DOPG),
- dipalmitoylphosphatidylglycerol (DPPG),
- palmitoyloleoylphosphatidylethanolamine (POPE),
- distearoyl-phosphatidyl-ethanolamine (DSPE),
- dipalmitoyl phosphatidyl ethanolamine (DPPE),
- dimyristoylphosphoethanolamine (DMPE),
- 1-stearoyl-2-oleoyl-phosphatidylethanol amine (SOPE),
- 1-stearoyl-2-oleoyl-phosphatidylcholine (SOPC),
- sphingomyelin,
- phosphatidylcholine,
- phosphatidylethanolamine,
- phosphatidylserine,
- phosphatidylinositol,
- phosphatidic acid,
- palmitoyloleoyl phosphatidylcholine,
- lysophosphatidylcholine, and
- lysophosphatidylethanolamine (LPE).

12. The lipid nanoparticle composition according to claim 1, further comprising a PEG lipid selected from the group consisting of PEG-modified phosphatidylethanolamine, PEG-modified phosphatidic acid, PEG-modified ceramide, PEG-modified dialkylamine, PEG-modified diacylglycerol, PEG-modified dialkylglycerol, and mixtures thereof.

13. The lipid nanoparticle composition according to claim 1, further comprising an ionic lipid,
wherein a molar ratio of the ionic lipid to the trehalose derivative compound is 1:0.7 to 1:1.3.

14. The lipid nanoparticle composition according to claim 13, further comprising a lithocholic acid derivative compound of the following Formula 3, a glycyrrhetinic acid derivative compound of the following Formula 7, or a diosgenin derivative compound represented by the following Formula 11 as a structural lipid,
wherein a molar ratio of the ionic lipid to the trehalose derivative compound to the structural lipid is 1:0.70-1.30:1.30-1.8:

[Formula 3]

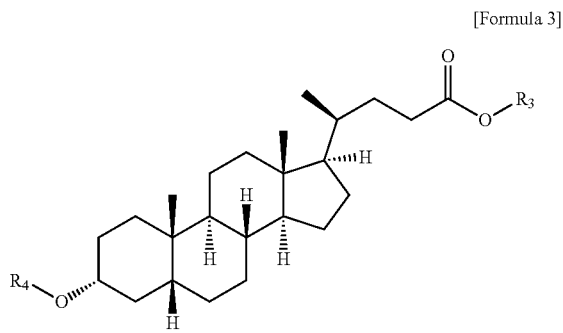

wherein $R_3$ and $R_4$ are each independently hydrogen or a saturated or unsaturated hydrocarbon having 2 to 20 carbon atoms,

[Formula 7]

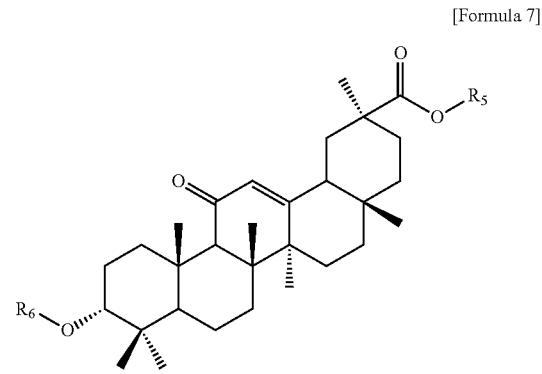

wherein $R_5$ and $R_6$ are each independently hydrogen or a saturated or unsaturated hydrocarbon having 2 to 20 carbon atoms,

[Formula 11]

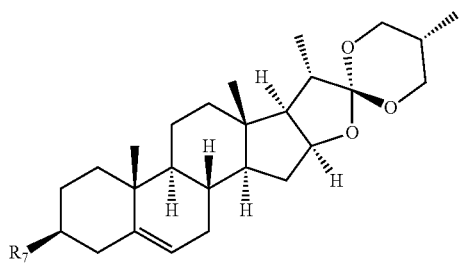

wherein R$_7$ includes —OH, —OMe, —NH$_2$, —NHMe, —NME2, —NME3, —SH, -glucose, methyl, or a saturated or unsaturated hydrocarbon having 2 to 20 carbon atoms.

15. The lipid nanoparticle composition according to claim 14, further comprising a phospholipid, wherein a molar ratio of the ionic lipid to the trehalose derivative compound to the structural lipid to the phospholipid is 1:0.70-1.30:1.30-1.80:0.35-0.45.

16. The lipid nanoparticle composition according to claim 1, further comprising a therapeutic and/or prophylactic agent.

17. The lipid nanoparticle composition according to claim 16, wherein the therapeutic and/or prophylactic agent is a vaccine or compound capable of inducing an immune response.

18. The lipid nanoparticle composition according to claim 16, wherein the therapeutic and/or prophylactic agent is nucleic acid selected from the group consisting of small interfering RNA (siRNA), asymmetric interfering RNA (aiRNA), microRNA (miRNA), dicer-substrate RNA (dsRNA), small hairpin RNA (shRNA), messenger RNA (mRNA), and mixtures thereof.

* * * * *